United States Patent [19]
Toda

[11] Patent Number: 5,694,979
[45] Date of Patent: Dec. 9, 1997

[54] METHOD AND APPARATUS FOR INSPECTING WOVEN CLOTH USING A PLURALITY OF PHOTOELECTRIC SENSORS

[75] Inventor: Masashi Toda, Kariya, Japan

[73] Assignee: Kabushiki Kaisha Toyoda Jidoshokki Seisakusho, Kariya, Japan

[21] Appl. No.: 588,833

[22] Filed: Jan. 19, 1996

[30] Foreign Application Priority Data

Jan. 26, 1995 [JP] Japan .................. 7-010930

[51] Int. Cl.⁶ .............. D03J 1/06; D03D 51/18; D06H 3/12; D06H 3/08
[52] U.S. Cl. .............. 139/1 B; 26/70; 250/559.01; 250/559.39; 242/534; 356/431; 139/370.2; 139/353; 139/351
[58] Field of Search ............ 139/1 B, 370.2, 139/353, 351; 26/70; 250/559.01, 559.39; 242/534, 432; 356/430, 431; 73/159

[56] References Cited

U.S. PATENT DOCUMENTS

| | | | |
|---|---|---|---|
| 4,738,284 | 4/1988 | Ishikawa et al. | 139/370.2 |
| 5,433,253 | 7/1995 | Toda et al. | 139/1 B |

FOREIGN PATENT DOCUMENTS

| | | | |
|---|---|---|---|
| 60-231850 | 11/1985 | Japan . | |
| 406033343 | 2/1994 | Japan | 139/1 B |
| 406033344 | 2/1994 | Japan | 139/1 B |
| 406041851 | 2/1994 | Japan | 139/1 B |
| 6065842 | 3/1994 | Japan | 139/370.2 |

*Primary Examiner*—Andy Falik
*Attorney, Agent, or Firm*—Brooks Haidt Haffner & Delahunty

[57] ABSTRACT

A woven cloth inspecting apparatus eliminates the influences of disturbances such as illuminating light and fly. At least two photoreceptor elements are arranged in the direction of the weft yarn of woven cloth. The photoreceptor elements detect different area of the woven cloth and they apply current signals to two respective current-to-voltage converters which convert the current signals into voltage signals which are fed to a difference calculating circuit. The difference calculating circuit calculates the difference between the values of the voltage signals received from the two current-to-voltage converters and supplies the obtained difference signal to a comparator which compares the received difference signal with a reference value preset by two reference value setting circuits. Exceeding the reference value is indicative of a defect in the warp. Alternatively the photoreceptor elements are arranged in the warp direction and detect defects in the weft. Also, photoreceptor elements can be located in both the weft and warp directions.

7 Claims, 16 Drawing Sheets

FIG. 3
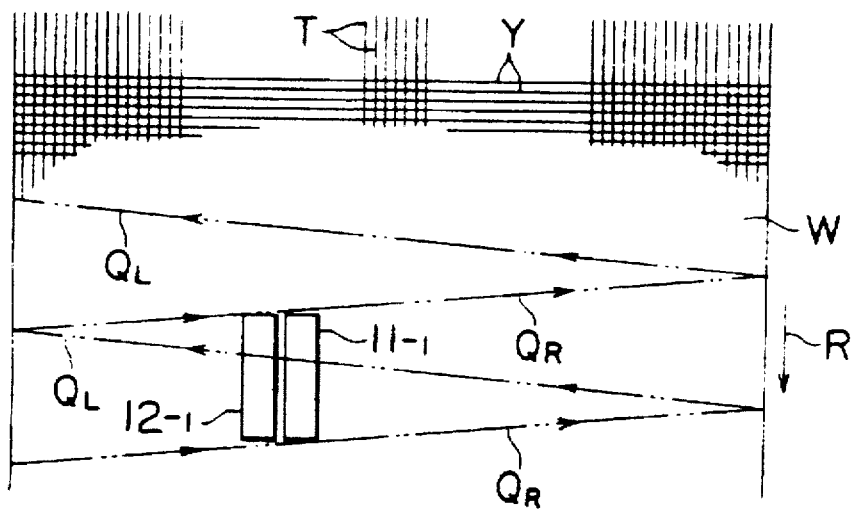
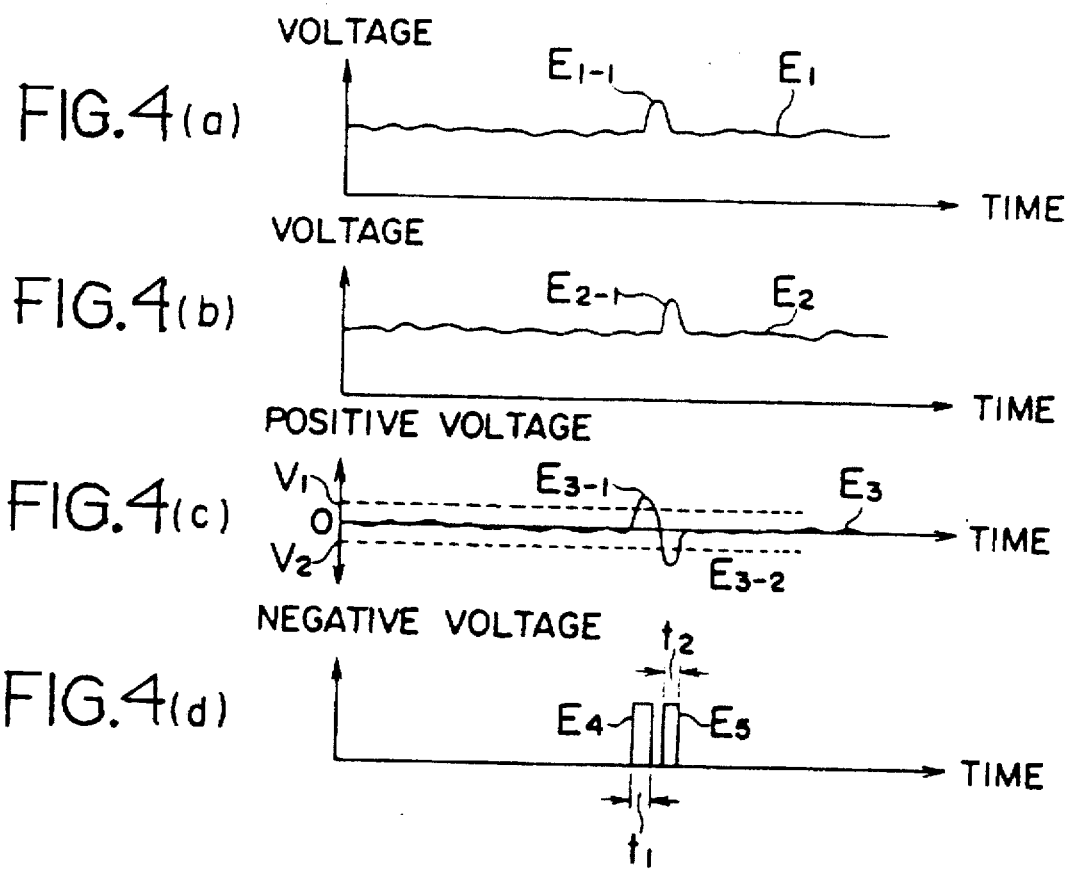
FIG.4(a)
FIG.4(b)
FIG.4(c)
FIG.4(d)

FIG. 7
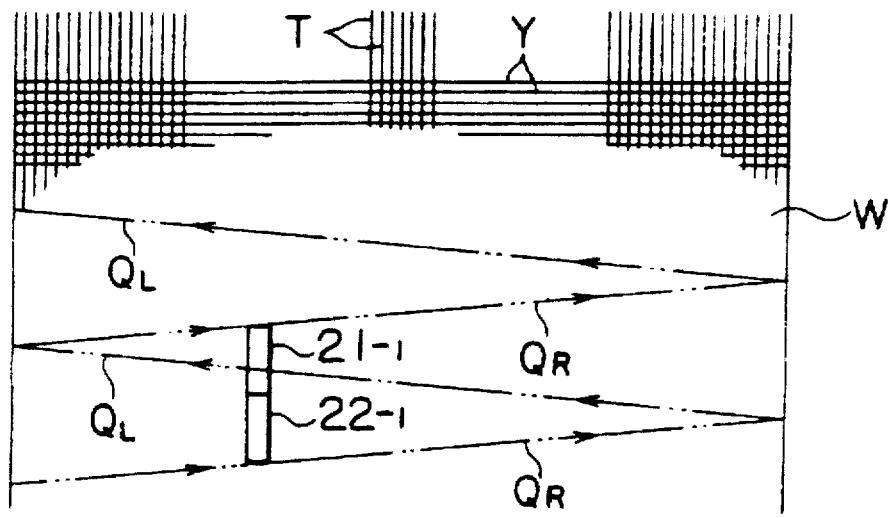
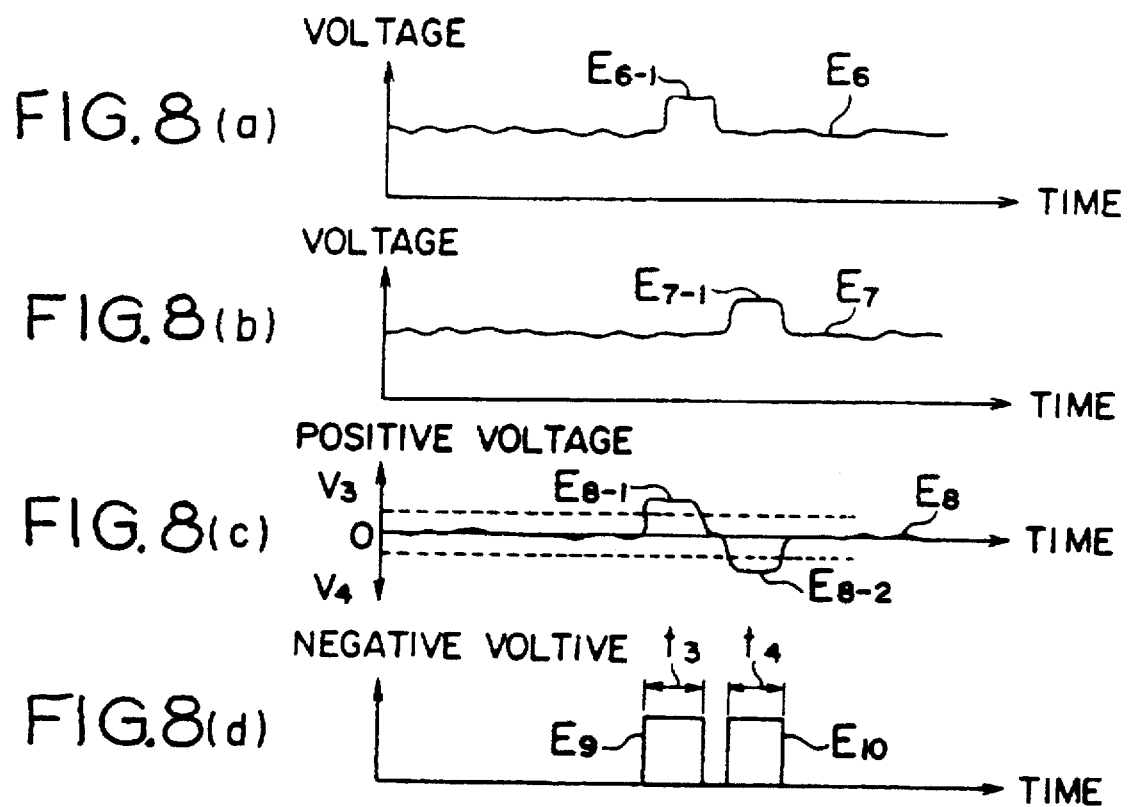

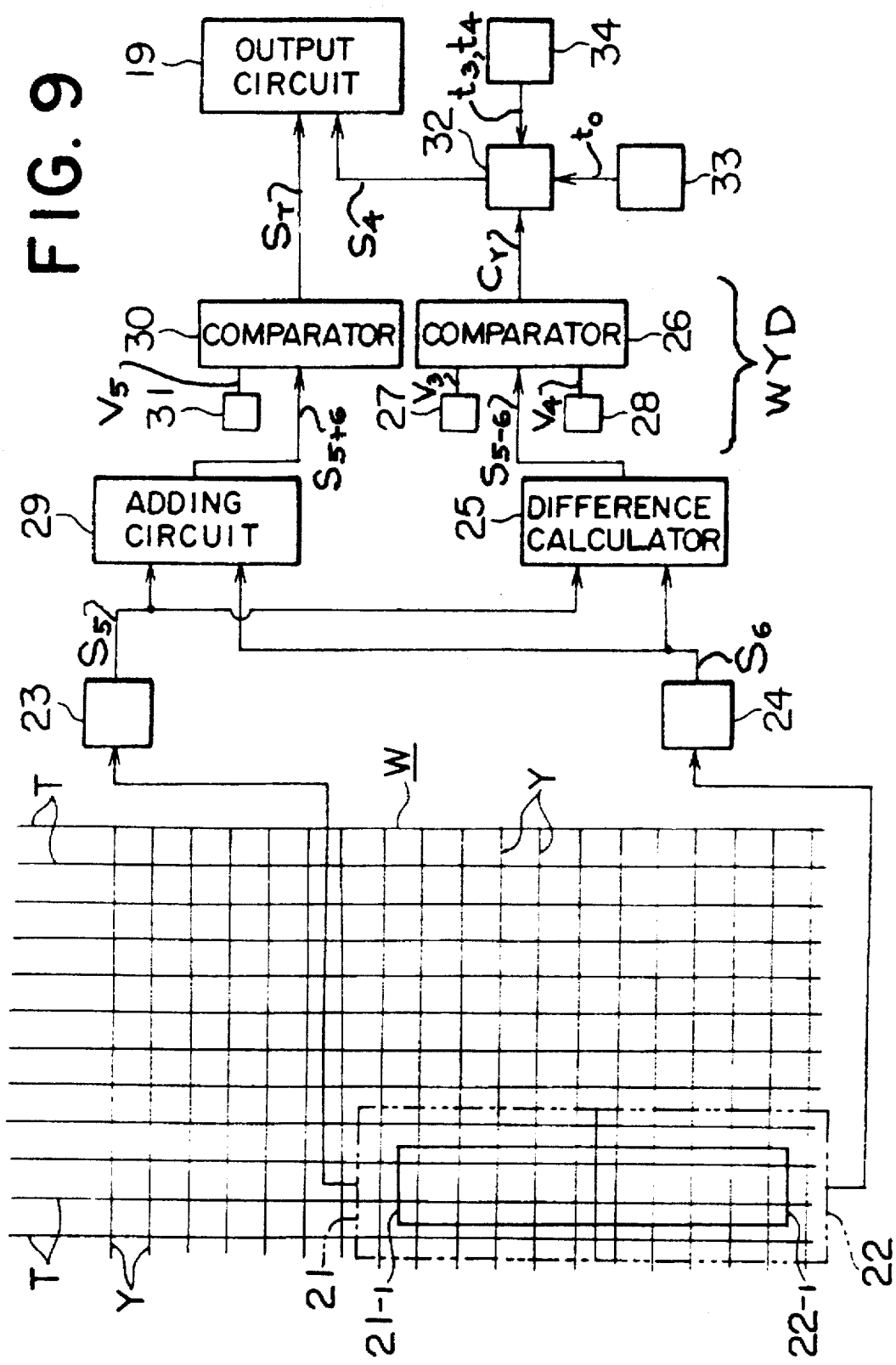

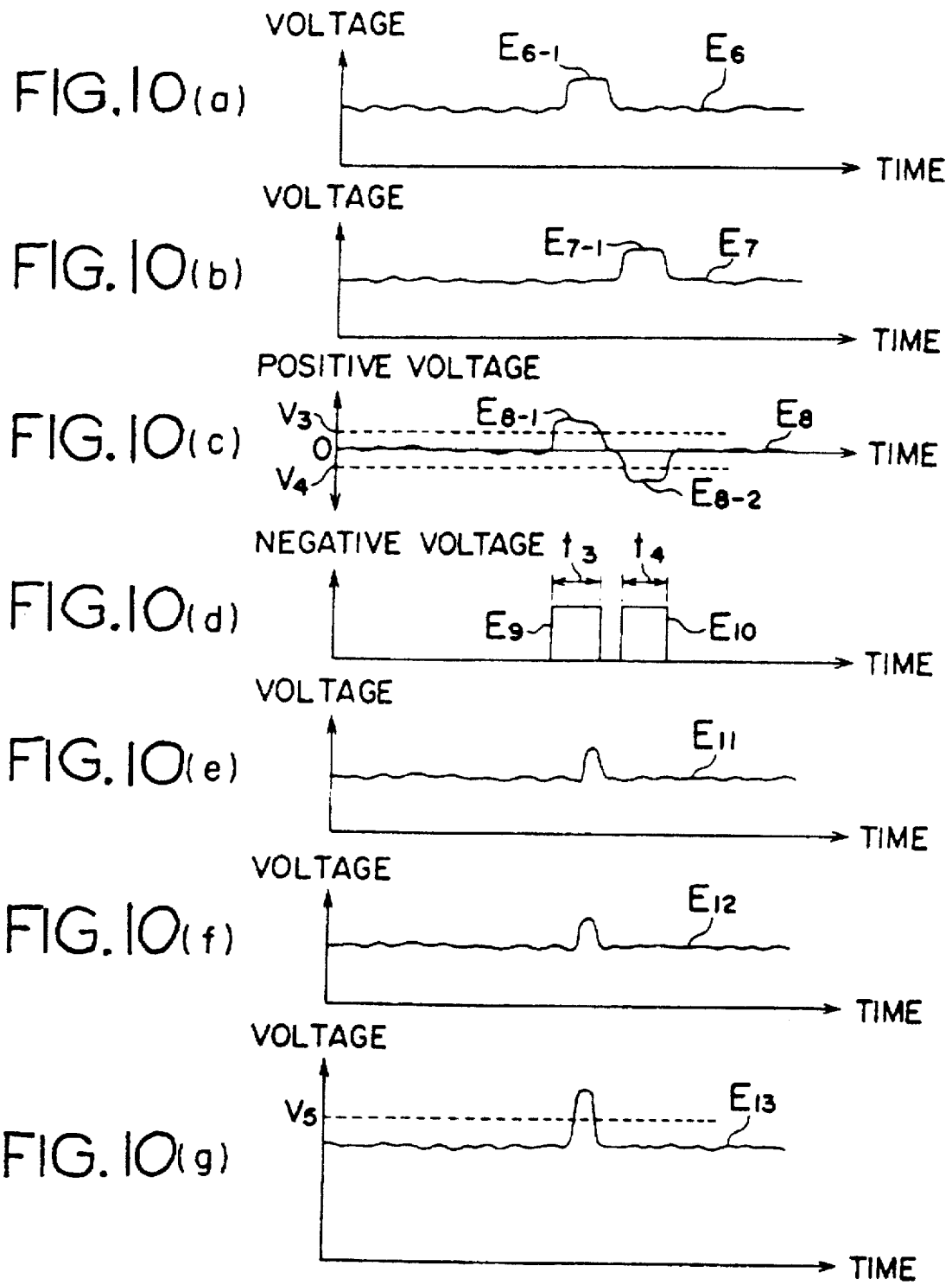

METHOD AND APPARATUS FOR INSPECTING WOVEN CLOTH USING A PLURALITY OF PHOTOELECTRIC SENSORS

BACKGROUND OF THE INVENTION

1. Field of the Invention

The present invention relates to a method and an apparatus for detecting a defect in cloth, which has been woven with warp and weft yarns, by using photoelectric sensors which issue electric signals based on the amount of received light.

2. Description of the Related Art

This type of apparatus for inspecting woven cloth has been disclosed in Japanese Patent Laid-Open No. 60-231850. In this apparatus, the light projected from a light source and reflected from the woven cloth is received by a photosensitive cell. The photosensitive cell issues an electric signal based on the amount of light received and the electric signal is evaluated by an evaluating unit.

The electric signal which has been converted in accordance with the amount of received light is generally evaluated by comparing the magnitude of the electric signal with a preset reference value. If the value of the electric signal is not more than the reference value, then the evaluation result indicates "normal"; if the value of the electric signal exceeds the reference value, then the evaluation result indicates "abnormal." The electric signal, however, is susceptible to the presence of illuminating light other than the inspecting apparatus or the presence of fly, causing changes in the electric signal. This prevents accurate inspection of the woven condition in the woven cloth with a resulting inspection error.

SUMMARY OF THE INVENTION

Accordingly, it is an object of the present invention to provide a method and an apparatus for inspecting woven cloth, which make it possible to eliminate the influences of disturbances such as illuminating light and fly.

To this end, according to one aspect of the present invention, a plurality of photoelectric sensors are disposed in the direction of one of the warp or the weft yarns, the difference between the electric signal from at least one of the plurality of photoelectric sensors and the electric signal from another photoelectric sensor is calculated, and a determining means determines whether a defect detection signal on the yarn other than the aforesaid one should be issued or not according to the calculation result.

According to another aspect of the present invention, there is provided an apparatus for inspecting woven cloth, which apparatus is equipped with a plurality of photoelectric sensors disposed in the direction of one of either the warp or the weft yarns, difference calculating means for calculating the difference between the electric signal from at least one of the plurality of photoelectric sensors and the electric signal from another photoelectric sensor, and determining means for determining whether a defect detection signal on the other yarn should be issued or not according to the calculation result.

With the arrangements stated above, the plurality of photoelectric sensors are disposed in the direction of either the warp or the weft yarns. The difference between the electric signal from at least one of the photoelectric sensors and the electric signal from another electric sensor is calculated and the obtained difference is compared with, for example, a preset reference value. The calculation of the difference eliminates the variations in the electric signals caused by disturbances such as illuminating light and fly. If the calculated difference exceeds the reference value, then the determining means issues the defect detection signal. When the plurality of photoelectric sensors is disposed in the direction of the weft yarn, the defect detection signal issued indicates that a defect in the ward yarn has been detected. When the plurality of photoelectric sensors is disposed in the direction of the warp yarn, the defect detection signal issued indicates that a defect in the weft yarn has been detected.

According to still another aspect of the present invention, there is provided an apparatus for inspecting woven fabric, which apparatus is equipped with a plurality of photoelectric sensors disposed in the direction of the warp yarn in the fabric, difference calculating means for calculating the difference between the electric signal from at least one of the plurality of photoelectric sensors and the electric signal from another photoelectric sensor, adding means for computing the sum of the electric signals from the plurality of photoelectric sensors, weft yarn defect determining means for determining whether a defect detection signal on the weft yarn should be issued or not according to the calculation result given by the difference calculating means, and warp yarn defect determining means for determining whether a defect detection signal on the warp yarn should be issued or not according to the calculation result given by the adding means.

With this arrangement, the difference between the electric signal from at least one of the plurality of photoelectric sensors disposed in the direction of the warp yarn and the electric signal from another photoelectric sensor is calculated by the difference calculating means and the sum of the electric signals from the photoelectric sensors is also calculated by the adding means. The calculation of the difference eliminates the variations in the electric signals caused by disturbances such as illuminating light or fly. The warp yarn defect determining means determines whether the defect detection signal on the warp yarn should be issued or not according to the calculation result given by the adding means. The weft yarn defect determining means determines whether the defect detection signal on the weft yarn should be issued or not according to the calculation result given by the difference calculating means.

According to a further aspect of the present invention, there is provided an apparatus for inspection of woven cloth, which apparatus is equipped with a plurality of photoelectric sensors which are disposed in the direction of the warp yarn and moved in the direction of the width of the woven cloth, difference calculating means for calculating the difference between the electric signal from at least one of the plurality of photoelectric sensors and the electric signal from another photoelectric sensor, adding means for computing the sum of the electric signals from the plurality of photoelectric sensors, warp yarn defect determining means for determining whether a defect detection signal on the warp yarn should be issued or not according to the calculation result given by the adding means, comparing means for comparing the value of the difference signal, which is obtained by the arithmetic operation performed by the difference calculating means, with a reference value and for issuing a time width fixation signal corresponding to the difference signal which exceeds the reference value, and pseudo defect determining means for determining whether the defect detection signal on the weft yarn should be issued or not according to the time width of the time width fixation signal.

With this arrangement, the detection by a plurality of photoelectric sensors and the calculation of the difference based on the electric signals are performed in the same manner as that described on the immediately preceding aspect of the present invention. The value of the difference signal obtained by the difference calculating means is compared with the reference value by the comparing means. The comparing means issues the time width fixation signal which corresponds to the difference signal exceeding the reference value. If the time width of the time width fixation signal is not less than the predetermined value, then the pseudo defect determining means issues the defect detection signal on the weft yarn. The time width of the time width fixation signal is detected in order to eliminate the influences exerted when a minor problem, which should not be defined as a defect, is detected on the warp yarn by the photoelectric sensors.

According to a still further aspect of the present invention, there is provided an apparatus for inspecting woven cloth, which apparatus is equipped with a plurality of photoelectric sensors, at least two of which are respectively disposed in the direction of the warp yarn and in the direction of the weft yarn, and moved in the direction of the width of the woven cloth, a first difference calculating means for calculating the difference between the electric signal from at least one of the plurality of photoelectric sensors which is disposed in the direction of the weft yarn among the plurality of the photoelectric sensors and the electric signal from another photoelectric sensor disposed in the direction of the weft yarn, a second difference calculating means for calculating the difference between the electric signal from at least one of the plurality of photoelectric sensors which is disposed in the direction of the warp yarn among the plurality of the photoelectric sensors and the electric signal from another photoelectric sensor disposed in the direction of the warp yarn, warp yarn defect determining means for determining whether the defect detection signal on the warp yarn should be issued or not according to the calculating result given by the first difference calculating means, comparing means for comparing the value of the difference signal, which is obtained by the second difference calculating means, with a reference value and for issuing a time width fixation signal corresponding to a difference signal exceeding the reference value, and a pseudo defect determining means for determining whether the defect detection signal on the weft yarn should be issued in accordance with the time width of the time width fixation signal.

With this arrangement, the detection by the plurality of photoelectric sensors disposed in the direction of the warp yarn, the calculation of the difference based on the electric signals, the comparison conducted by the comparing means according the calculation result, and the decision made by the pseudo defect determining means according to the comparison result are all performed in the same manner as those described on the immediately preceding aspect of the present invention. The detection by the plurality of photoelectric sensors disposed in the direction of the weft yarn, the calculation of the difference based on the electric signals, and the decision made by the warp yarn defect determining means according to the calculation result are performed in order to check the warp yarn for any defect.

BRIEF DESCRIPTION OF THE DRAWINGS

FIG. 3 is a top plan view illustrative of a scanning area in the detectable range;

FIGS. 4(a) through (d) are graphs illustrative of the signal processing implemented through the control circuit;

FIG. 7 is a top plan view illustrative of the scanning area in the detectable range;

FIGS. 8(a) through (d) are graphs illustrative of the signal processing implemented through the control circuit;

FIG. 9 shows the combination of the control circuit and the detectable range on woven cloth which are illustrative of a third embodiment;

FIGS. 10(a) through (g) are graphs illustrative of the signal processing implemented through the control circuit;

DESCRIPTION OF THE PREFERRED EMBODIMENTS

The first embodiment, which has embodied the present invention in a woven cloth inspecting apparatus mounted on a weaving machine, will be described in conjunction with FIGS. 1 to 4.

Figure 1:
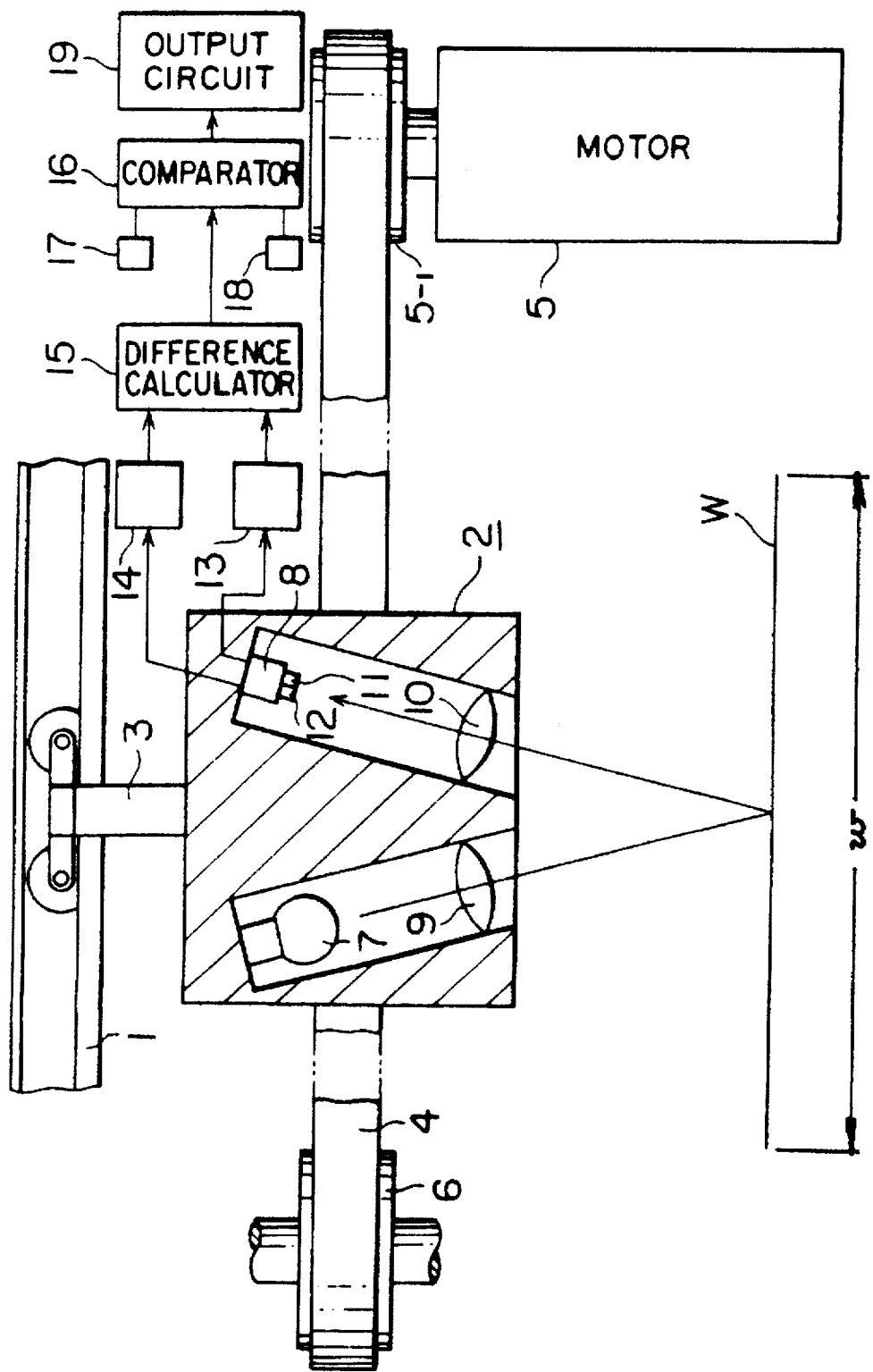
FIG. 1 shows a combination of an essential section and a control circuit illustrative of a first embodiment of the present invention.
Figure 2:
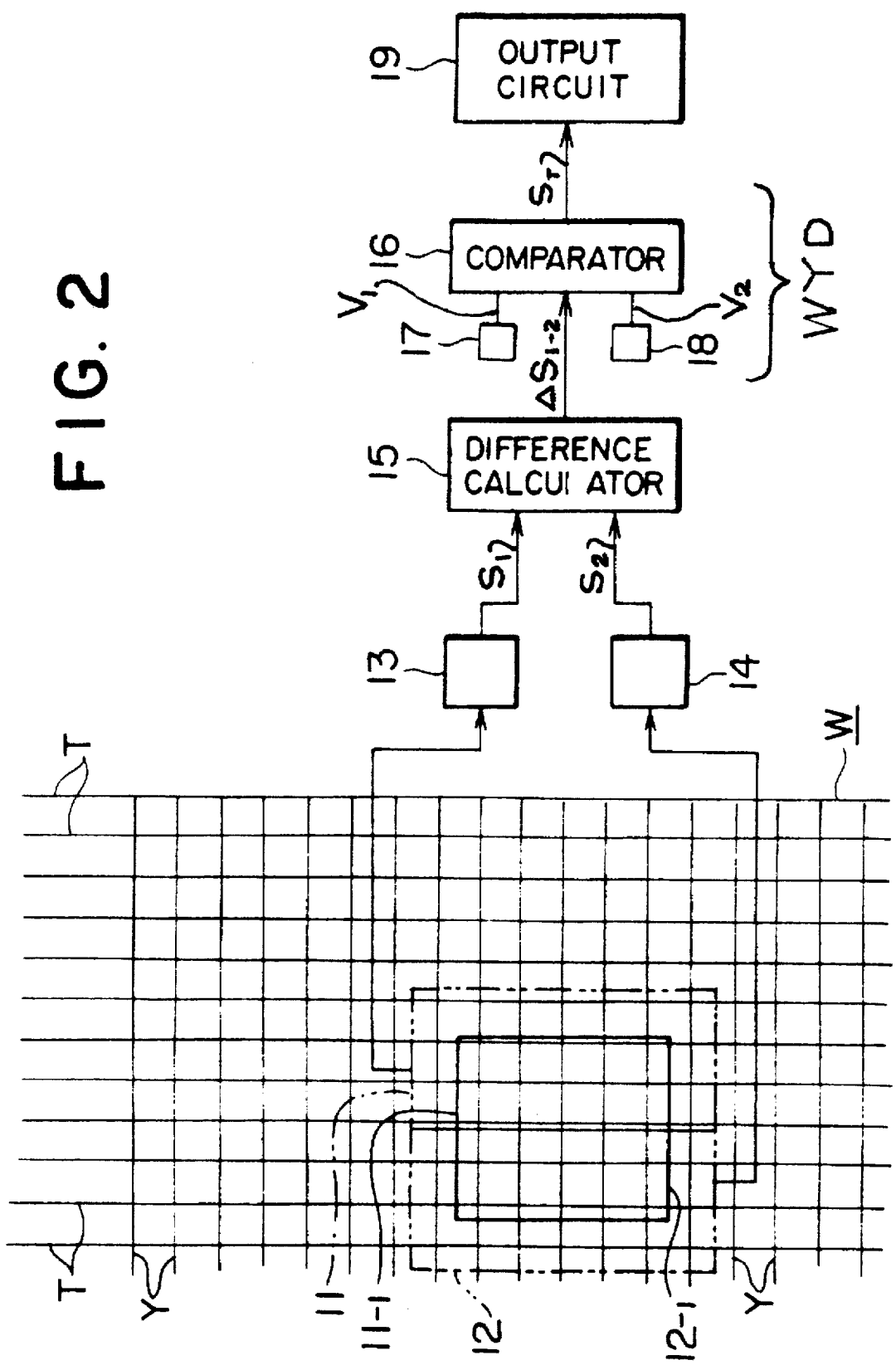
FIG. 2 shows the combination of the control circuit and a detectable range on woven cloth.

As shown in FIG. 1, a rail 1 is provided above woven cloth W in the direction of the width w of the woven cloth W. A sensor head 2 is suspended from the rail 1 via a guide assembly 3. The guide assembly 3 is allowed to move along the rail 1. An endless belt 4 is connected to the sensor head 2 and is mounted on a drive pulley 5-1 and a guide pulley 6. The endless belt 4 is rotated in a reciprocating manner by the reciprocating drive of a motor 5; and thus the sensor head 2 reciprocates along the rail 1.

The sensor head 2 incorporates a projector 7, a photoreceptor 8, and optical systems 9, 10. The light emitted from the projector 7 illuminates the woven cloth W via the optical system 9 and the light reflected from the woven cloth W is received by the photoreceptor 8 via the optical system 10. The reciprocative range of the sensor head 2 defines the range in which the light emitted from the projector 7 scans across the woven width w of the woven cloth W.

As shown in FIG. 1, the photoreceptor 8 is equipped with a pair of photoreceptor elements 11, 12 which are arranged in the direction Y, i.e. of the weft yarn, of woven cloth W, as seen in FIG. 3. Reference numeral 11-1 shown in FIG. 2 and FIG. 3 denotes the detection range of the photoreceptor element 11 on the woven cloth W; and reference numeral 12-1 denotes the detection range of the photoreceptor element 12 on the woven cloth W. Warp yarn T of woven cloth W are passed between the dents of a reed, not shown, on a basis of a few yarns; and the width of the detection ranges 11-1 and 12-1 in the direction of weft yarn Y is set approximately equal to the pitch of the dents of the reed. The width of the detection ranges 11-1 and 12-1 in the direction of warp yarn T is set so that it is a few times as large as the width of the ranges in the direction of weft yarn Y. The area enclosed by the parallel right-pointing arrows $Q_r$ in FIG. 3 indicates the area of the detection ranges 11-1, 12-1 on woven cloth W which is swept by the sensor head 2 when it moves in the right hand direction. Likewise, the area enclosed by the parallel left-pointing arrows $Q_L$ indicates the area of the detection ranges 11-1, 12-1 on woven cloth W which is swept by the sensor head 2 when it moves in the left hand direction. Woven cloth W moves in the direction of arrow R.

The photoreceptor elements 11, 12 convert received light into a current. The current signal obtained by the conversion is an electric signal based on the amount of received light. The photoreceptor element 11 supplies the current signal to a current-to-voltage converter 13; and the photoreceptor element 12 supplies the current signal to a current-to-voltage converter 14. The current-to-voltage converters 13, 14 convert the current signal into voltage signals $S_1$, $S_2$ which are then supplied to a difference calculating circuit 15. The difference calculating circuit 15 calculates the difference between the values of voltage signals $S_1$, $S_2$ received from the two current-to-voltage converters 13, 14. In the arithmetic operation, the value of voltage signal $S_2$ is subtracted from the value of voltage signal $S_1$. The difference calculating circuit 15 applies difference signal $\Delta S_{1-2}$ obtained by the arithmetic operation to a comparator 16. The comparator 16 compares difference signal $\Delta S_{1-2}$, which has been received, with reference values $V_1$, $V_2$ which have been set beforehand by reference value setting circuits 17, 18. Reference value $V_1$, is positive; reference value $V_2$ is negative. If the value of difference signal $\Delta S_{1-2}$ is out of the range defined by $[V_1, V_2]$, then the comparator 16 issues defect detection signal $S_T$ to an output circuit 19. If the value of difference signal $\Delta S_{1-2}$ is within the range defined by $[V_1, V_2]$, then the comparator 16 does not issue defect detection signal $S_T$ to the output circuit 19. The comparator 16 together with the reference value setting circuits 17, 18 constitute the warp yarn defect determining means WYD. The output circuit 19 issues a weaving halt signal, a failure indication signal, etc. in accordance with defect detection signal $S_T$ which it receives.

Curve $E_1$ of FIG. 4(a) indicates voltage signal $S_1$, issued from the current-to-voltage converter 13; and curve $E_2$ of FIG. 4(b) indicates voltage signal $S_2$ issued from the current-to-voltage converter 14. Curve $E_3$ of FIG. 4(c) indicates difference signal $\Delta S_{1-2}$ obtained by subtracting the value of curve $E_2$ from the value of curve $E_1$. Square waves $E_4 E_5$ of FIG. 4(d) denote defect detection signal $S_T$ issued from the comparator 16. The axes of abscissa in FIG. 4(a) through FIG. 4(d) all denote time; and the axes of ordinate in FIG. 4(a) through FIG. 4(c) all denote voltage.

Projection $E_{1-1}$ of curve $E_1$ denotes a problem with the warp yarn detected by the photoreceptor element 11. Projection $E_{2-1}$ of curve $E_2$ denotes a problem with the warp yarn detected by the photoreceptor element 12. The time difference between projections $E_{1-1}$ and $E_{2-1}$ is caused by arranging the photoreceptor elements 11, 12, which move in the direction of weft Y, in the direction of the weft yarn Y. Projection $E_{3-1}$ of curve $E_3$ denotes the difference between projection $E_{1-1}$, and the nearly flat portion of curve $E_2$ corresponding to the time area of projection $E_{1-1}$. Projection $E_{3-2}$ of curve $E_3$ denotes the difference between projection $E_{2-1}$, and the nearly flat portion of curve $E_1$ corresponding to the time area of projection $E_{2-1}$. Time width $t_1$ of square wave $E_4$ corresponds to the time width of projection $E_{3-1}$ which exceeds reference value $V_1$ on the positive side; time width $t_2$ of square wave $E_5$ corresponds to the time width of projection $E_{3-2}$ which exceeds reference value $V_2$ on the negative side.

Warp yarn T is passed between adjoining dents on the basis of a predetermined number of yarn. For example, it sometimes happens that the number of warp yarns set between certain adjoining dents is less than the predetermined value whereas the number of warp yarns set between different adjoining dents is more than the predetermined value. If this situation continues, then a "warp rib" is formed on the woven cloth, resulting in defective woven cloth. The range of the detection ranges 11-1, 12-1 of the photoreceptor elements 11, 12 in the direction of weft yarn Y is set approximately to the pitch of the dents; therefore, the amount of light received by the photoreceptor elements 11, 12 differs between the rib portion and the normal portion on woven cloth W. This causes changes in voltage signals $S_1$, $S_2$ shown by projections $E_{1-1}$, $E_{2-1}$ of curves $E_1$, $E_2$.

The output of defect detection signal $S_T$ denoted by square waves $E_4$, $E_5$ is determined according to the result of the comparison between difference signal $\Delta S_{1-2}$ of voltage signals $S_1$, $S_2$ obtained from the photoreceptor elements 11,12 and reference values $V_1$ and $V_2$. Disturbances including the presence of illuminating light other than the cloth inspecting apparatus and the presence of fly cause changes in the voltage signals $S_1$, $S_2$. This means that voltage signals $S_1$, $S_2$ contain a change component caused by such disturbances; therefore, such changes in voltage signals $S_1$, $S_2$ prevent accurate determination of a woven condition of the woven cloth and any attempt which might be made to check the woven cloth for a defect according to the result of the comparison between voltage signals $S_1$, $S_2$ and the reference values $V_1$, $V_2$ would result in an inspection error. On the other hand, in difference signal $\Delta S_{1-2}$ which indicates the difference between voltage signals $S_1$ and $S_2$, the change component attributable to the disturbances which has been included in the voltage signals is almost offset. Hence, difference signal $\Delta S_{1-2}$ accurately reflects the presence of a trouble with warp yarn T and therefore the comparison between difference signal $\Delta S_{1-2}$ and reference values $V_1$, $V_2$ enhances the accuracy of inspecting warp yarn for a defect.

Figure 5:
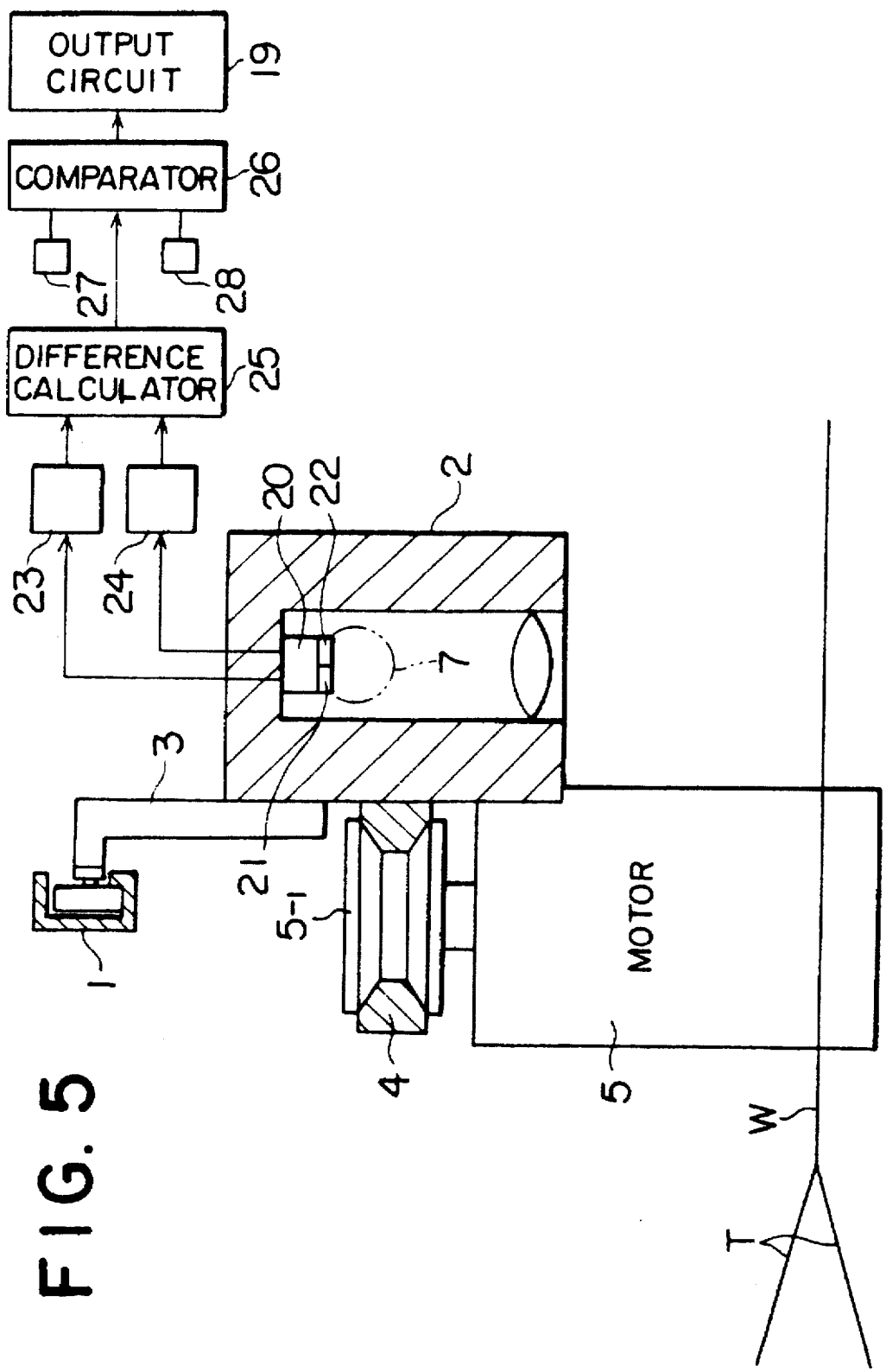
FIG. 5 shows the combination of an essential section and a control circuit illustrative of a second embodiment.
Figure 6:
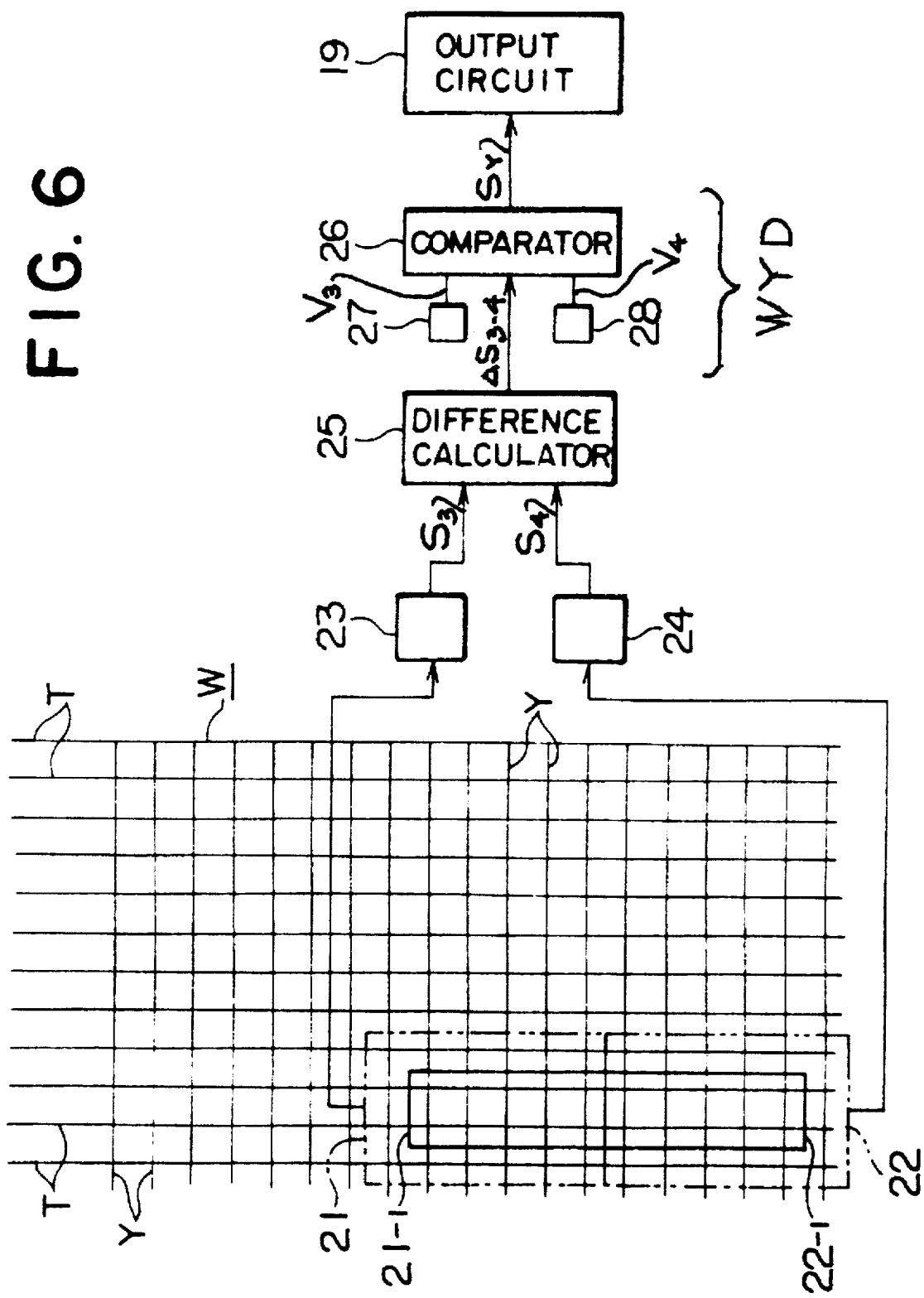
FIG. 6 shows the combination of the control circuit and the detectable range on woven cloth.

The second embodiment shown in FIGS. 5 to 8 will now be described. The same component members as those of the first embodiment are assigned the same reference numerals and the detailed description thereof will be omitted. As shown in FIG. 5, a photoreceptor of the second embodiment is equipped with a pair of photoreceptor elements 21, 22; and the photoreceptor elements 21, 22 are disposed in series in the direction of warp yarn T of the woven cloth W. Reference numeral 21-1 shown in FIGS. 6 and 7 denotes the detection range of the photoreceptor element 21 on the woven cloth W; and reference numeral 22-1 denotes the detection range of the photoreceptor element 22 on the woven cloth W. The width of the detection ranges 21-1 and 22-1 in the direction of weft yarn Y is set approximately to the pitch of the dents of the reed. The width of the detection ranges 21-1 and 22-1 in the direction of warp yarn T is set so that it is a few times as large as the width in the direction of weft yarn Y. The area enclosed by the right-pointing parallel arrows $Q_R$ in FIG. 7 indicates the area of the detection ranges 21-1, 22-1 on the woven cloth W which is swept by the sensor head 2 when it moves to the right. Likewise, the area enclosed by the left-pointing parallel arrows $Q_l$ indicates the area of the detection ranges 21-1, 22-1 on the woven cloth W which is swept by the sensor head 2 when it moves to the left.

The photoreceptor elements 21, 22 (FIG. 6) convert received light into a current. The current signal obtained by the conversion from light provides an electric signal based on the amount of received light. The photoreceptor element 21 supplies the current signal to a current-to-voltage converter 23: and the photoreceptor element 22 supplies the current signal to a current-to-voltage converter 24. The current-to-voltage converters 23, 24 convert the current signal into voltage signals $S_3$, $S_4$ which are then supplied to a difference calculating circuit 25. The difference calculating circuit 25 subtracts the value of voltage signal $S_4$ from the value of voltage signal $S_3$. The difference calculating circuit 25 applies signal difference signal $\Delta S_{3-4}$ obtained by the arithmetic operation to a comparator 26. The comparator 26 compares difference signal $\Delta S_{3-4}$, which has been received, with reference values $V_3$, $V_4$ which have been set beforehand by reference value setting circuits 27, 28. Reference value $V_3$ is positive: reference value $V_4$ is negative. If the value of difference signal $\Delta S_{3-4}$ is out of the range defined by $[V_3, V_4]$, then the comparator 26 issues defect detection signal $S_Y$ to an output circuit 19. If the value of difference signal $\Delta S_{3-4}$ is within the range defined by $[V_3, V_4]$, then the comparator 26 does not issue defect detection signal $S_Y$ to the output circuit 19. The comparator 26 together with the reference value setting circuits 27, 28 constitute the weft yarn defect determining means WYD.

Curve $E_6$ of FIG. 8(a) indicates voltage signal $S_3$ issued from the current-to-voltage converter 23; curve $E_7$ of FIG. 8(b) indicates voltage signal $S_4$ issued from the current-to-voltage converter 24. Curve $E_8$ of FIG. 8(c) indicates difference signal $\Delta S_{3-4}$ obtained by subtracting the value of curve $E_7$ from the value of curve $E_6$. Square waves $E_9$, $E_{10}$ of FIG. 8(d) denote defect detection signal $S_Y$ issued from the comparator 26. The axes of abscissa in FIG. 8(a) through FIG. 8(d) all denote time: the axes of ordinate in FIG. 8(a) through FIG. 8(c) all denote voltage.

Projection $E_{6-1}$ of curve $E_6$ denotes a problem with weft yarns detected by the photoreceptor element 21. Projection $E_{7-1}$ of curve $E_7$ denotes a problem with weft yarns detected by the photoreceptor element 22. The time difference between projections $E_{6-1}$ and $E_{7-1}$ is caused by arranging the photoreceptor elements 21, 22, which move in the direction of weft yarns T, in the direction of warp yarns T. Projection $E_{8-1}$ of curve $E_8$ denotes the difference between projection $E_{6-1}$ and the nearly flat portion of curve $E_7$ corresponding to the time area of projection $E_{6-1}$. Projection $E_{8-2}$ of curve $E_8$ denotes the difference between projection $E_{7-1}$ and the nearly flat portion of curve $E_6$ corresponding to the time area of projection $E_{7-1}$. Time width $t_3$ of square wave $E_9$ corresponds to the time width of projection $E_{8-1}$ which is larger than reference value $V_3$; time width $t_4$ of square wave $E_{10}$ corresponds to the time width of projection $E_{8-2}$ which is smaller than reference value $V_4$.

If weft Y has a defect such as a loop or broken yarn, then the amount of light received by the photoreceptor elements 21, 22 differs between the defective portion and the normal portion on the woven cloth W. This causes changes in voltage signals $S_3$, $S_4$ shown by projections $E_{6-1}$, $E_{7-1}$ of curves $E_6$, $E_7$. The output of defect detection signal $S_Y$ denoted by square waves $E_9$, $E_{10}$ is determined according to the result of the comparison between difference signal $\Delta S_{3-4}$ of voltage signals $S_3$, $S_4$ obtained from the photoreceptor elements 21, 22 and reference values $V_3$ and $V_4$. Voltage signals $S_3$, $S_4$ contain a change component attributable to disturbances. However, in difference signal $\Delta S_{3-4}$ which indicates the difference between voltage signals $S_3$ and $S_4$, the change component due to the disturbances which has been included in the voltage signals is almost offset. Furthermore, since the photoreceptor elements 21, 22 are arranged in series in the direction of the warp yarn, the change component in the electric signals caused by the light reflected from the warp yarn is also offset. As a result, difference signal $\Delta S_{3-4}$ accurately reflects the presence of a trouble with weft yarn Y and therefore the comparison between difference signal $\Delta S_{3-4}$ and reference values $V_3$, $V_4$ enhances the accuracy of inspecting the weft yarns for a defect.

The third embodiment shown in FIGS. 9 and 10 will now be described. The same component members as those of the second embodiment are assigned the same reference numerals and the detailed description thereof will be omitted. As shown in FIG. 9, the photoreceptor elements 21, 22 are disposed in series in the direction of warp yarn T of the woven cloth W as in the case of the second embodiment. The photoreceptor element 21 supplies a current signal to the current-to-voltage converter 23; the photoreceptor element 22 supplies a current signal to the current-to-voltage converter 24. The current-to-voltage converter 23 converts the current signal to a voltage signal $S_5$ which is supplied to an adding circuit 29 and the difference calculating circuit 25. The current-to-voltage converter 24 converts a current signal to voltage signal $S_6$ which is supplied to the adding circuit 29 and the difference calculating circuit 25. The adding circuit 29 adds voltage signals $S_5$, $S_6$; the difference calculating circuit 25 subtracts the value of voltage signal $S_6$ from the value of voltage signal $S_5$. The adding circuit 29 sends sum signal $S_{5+6}$ obtained from the arithmetic operation to a comparator 30. The comparator 30 compares sum signal $S_{5+6}$, which has been received, with reference value $V_5$ which has been set beforehand by a reference value setting circuit 31. If the value of sum signal $S_{5+6}$ exceeds reference value $V_5$, then the comparator 30 issues defect detection signal $S_T$ to the output circuit 19. If the value of sum signal $S_{5+6}$ is smaller than reference value $V_5$, then the comparator 30 does not issue defect detection signal $S_T$ to the output circuit 19. The difference calculating circuit 25 sends difference signal $\Delta S_{5-6}$, which has been obtained from the arithmetic operation, to the comparator 26.

The adding circuit 29 combines the photoreceptor elements 21, 22 into one piece to expand the detection range in the direction of warp yarn T. Such expansion of the detection range enhances the capability of detecting the warp yarn for a defect.

The graphs shown in FIGS. 10(a) to (d) are identical to the graphs shown in FIGS. 8(a) to (d). Curve $E_{11}$ of FIG. 10(e) shows an example of voltage signal $S_5$ issued from the current-to-voltage converter 23. Curve $E_{12}$ of FIG. 10(f) shows an example of voltage signal $S_6$ issued from the current-to-voltage converter 24. Curve $E_{13}$ of FIG. 10(g) denotes sum signal $S_{5+6}$ obtained by adding curve $E_{11}$ and curve $E_{12}$.

The comparator 26 compares difference signal $\Delta S_{5-6}$ with reference values $V_3$, $V_4$. If the value of difference signal $\Delta S_{5-6}$ is out of the range of $[V_3, V_4]$, then the comparator 26 sends out confirmation request signal $C_Y$ to a counter 32. If the value of difference signal $\Delta S_{5-6}$ is within the range of $[V_3, V_4]$, then the comparator 26 does not send out confirmation request signal $C_Y$ to the counter 32. Signal-connected to the counter 32 are a latching circuit 33 and a clock 34. Time $t_0$ is stored in the latching circuit 33. The counter 32 decides whether defect detection signal $S_Y$ should be issued or not according to the result of the comparison between the time measured by the clock 34 and preset time $t_0$.

Preset time $t_0$ is decided as shown below. Time width $t_Y$ for detecting a defect in weft yarn and detection width $t_T$ for a defect in warp yarn are expressed by equations (1) and (2) given below:

$$t_Y = (L_T + D_Y)/V_T \quad (1)$$

$$t_T = (L_Y + D_T)/V_Y \quad (2)$$

where $L_T$ denotes the width of detection ranges 21-1 and 22-1 in the direction of warp yarn T; $L_Y$ denotes the width of detection ranges 21-1, 22-1 in the direction of weft yarn Y; $D_Y$ denotes the width of defect in weft yarn; and $D_T$ denotes the width of defect in warp yarn. $V_T$ indicates the relative moving velocity of the detection ranges 21-1, 22-1 in the direction of warp yarn T with respect to the woven cloth W; $V_Y$ indicates the relative moving velocity of the detection ranges 21-1, 22-1 in the direction of weft yarn Y with respect to the woven cloth W. Relative moving velocity is the moving velocity of the woven cloth W.

Whereas the aforesaid warp yarn rib can be defined as a major defect in warp yarn, there are cases where minute gaps, which should not be defined as a defect, are produced intermittently. Such a gap (hereinafter referred to as "a pseudo defect") tends to occur when the warp yarn density is high. In the case of such a pseudo defect, the width in the direction of weft yarn Y is equivalent approximately to one pitch of warp yarn T at the largest and it is smaller than width $L_Y$ which is set to about the dent interval. Hence, if width $D_T$ in equation (2) is the width of the pseudo defect, then substituting width $D_T$ in equation (2) with $L_Y$ leads to equation (3) given below:

$$t_T > 2L_Y/V_Y \quad (3)$$

Assigning zero to $D_Y$ in equation (1) leads to equation (4):

$$t_Y > L_T/V_T \quad (4)$$

From equations (3) and (4), equation (5) will be given:

$$2L_Y/V_x \leq LT/VT \quad (5)$$

Modifying equation (5) leads to equation (6):

$$V_Y \geq (2L_Y/L_T)V_T \quad (6)$$

Thus, equation (7) holds when the sensor head 2 is moved at moving velocity $V_Y$ which satisfies the conditions of equation (6):

$$t_Y < t_T \quad (7)$$

Time width $t_T$ in equation (7) relates to the pseudo defect whereas time width $t_Y$ relates to the defect in weft yarn. Hence, moving the sensor head 2 at moving velocity $V_Y$, which satisfies the conditions of equation (6), makes it possible to identify weft yarn defects and pseudo defects. For the purpose of such identification, $L_T/V_T$ in equations (4) and (5) is decided as preset time to and time width $t_Y$ exceeds preset time $t_0$, then square wave $E_9$ or $E_{10}$ leading to time width $t_Y$ represents the actual weft yarn defect. Square waves $E_9$, $E_{10}$ provide time width confirmation signals representing time widths $t_3$, $t_4$. The counter 32 which constitutes the pseudo defect determining means together with the latching circuit 33 and the clock 34 issues defect detection signal $S_Y$ if time width $t_3$ of square wave $E_9$ or time width $t_4$ of square wave $E_{10}$ exceeds preset time $t_0$. Such an identifying method makes it possible to distinguish a pseudo defect from a weft yarn defect, thereby enabling higher accuracy of inspection for weft yarn defects.

Figure 11:
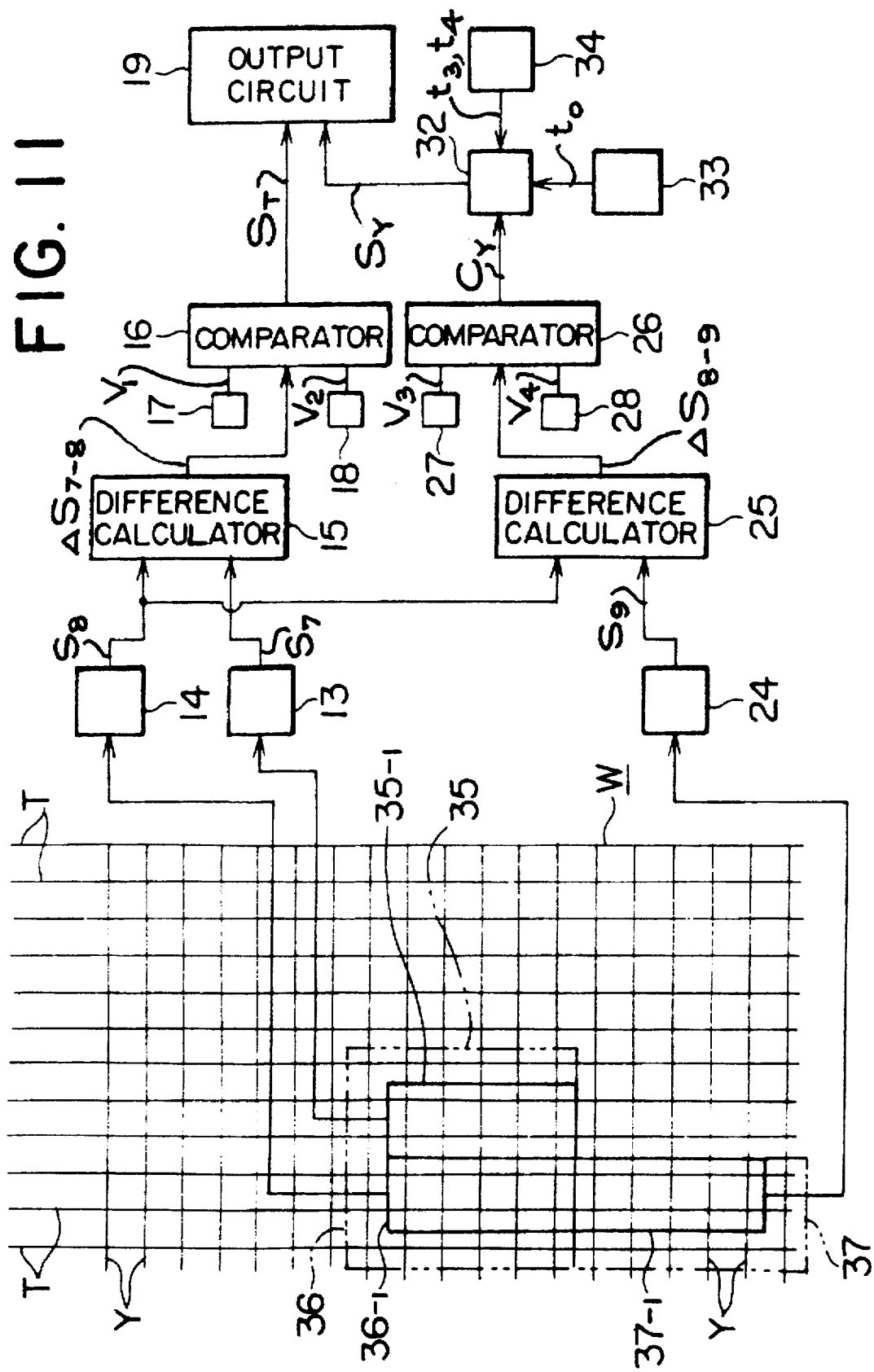
FIG. 11 shows the combination of the control circuit and the detectable range on woven cloth which are illustrative of a fourth embodiment.
Figure 12:
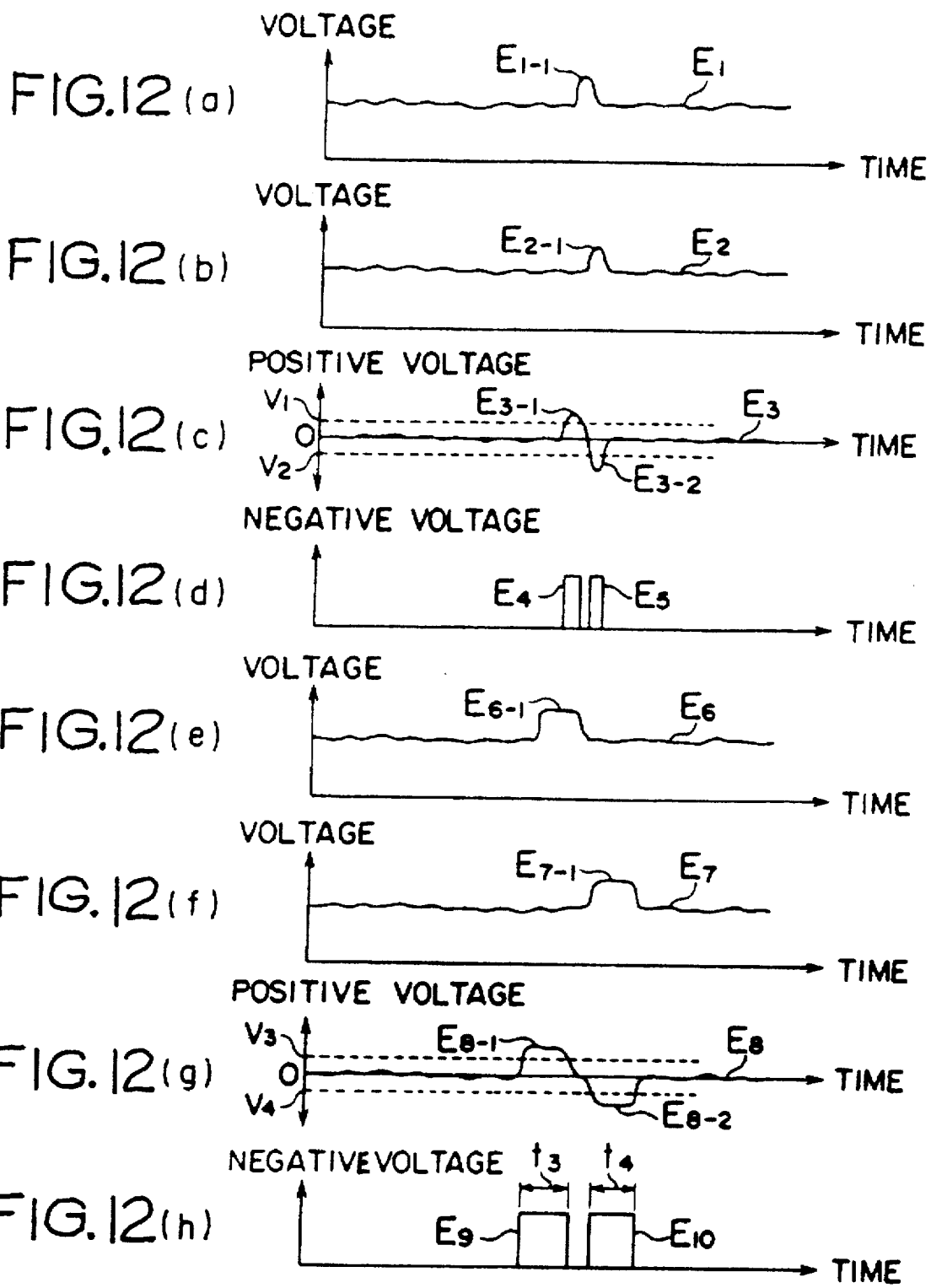
FIGS. 12(a) through (h) are graphs illustrative of the signal processing implemented through the control circuit.

The fourth embodiment of FIGS. 11 and 12 will now be described. The same component members as those of the third embodiment are assigned the same reference numerals and the detailed description thereof will be omitted. As shown in FIG. 11, the photoreceptor elements 35, 36 are disposed in series in the direction of weft yarn Y of the woven cloth W as in the case of the first embodiment. The photoreceptor elements 36, 37 are disposed in series in the direction of warp yarn T of the woven cloth W as in the case of the second embodiment. Reference numerals 35-1, 36-1, and 37-1 denote the detection ranges of the individual photoreceptor elements 35, 36, and 37, respectively. The photoreceptor element 35 sends out current signals to the current-to-voltage converter 13. The current-to-voltage converter 13 converts the current signal to voltage signal $S_7$ which is then supplied to the difference calculating circuit 15. The current-to-voltage converter 14 converts the current signal received from the photoreceptor element 36 to voltage signal $S_8$ which is then supplied to the difference calculating circuits 15, 25. The difference calculating circuit 15 subtracts the value of voltage signal $S_8$ from the value of voltage signal $S_7$. The difference calculating circuit 15 applies difference signal $\Delta S_{7-8}$ obtained from the arithmetic operation to the comparator 16. The current-to-voltage converter 24 converts the current signal received from the photoreceptor element 37 to voltage signal $S_9$ which is sent to the difference calculating circuit 25. The difference calculating circuit 25 supplies difference signal $\Delta S_{8-9}$ obtained from the arithmetic operation to the comparator 26.

The graphs shown in FIGS. 12(a) to (d) are identical to the graphs shown in FIGS. 4(a) to (d). The graphs shown in FIGS. 12(e) to (h) are identical to the graphs shown in FIGS. 8(a) to (d). Curve of FIG. 12(a) represents a signal issued from the current-to-voltage converter 13; and curve $E_2$ of FIG. 12(b) represents a signal issued from the current-to-voltage converter 14. Curve $E_6$ of FIG. 12(e) represents a signal issued from the current-to-voltage converter 14; and curve $E_7$ of FIG. 12(f) represents a signal issued from the current-to-voltage converter 24.

The comparator 16 compares the received difference signal $\Delta S_{7-8}$ with reference values $V_1$, $V_2$. If the value of difference signal $\Delta S_{7-8}$ is out of the range defined by $[V_1, V_2]$, then the comparator 16 issues defect detection signal $S_T$ to the output circuit 19. If the value of difference signal $\Delta S_{7-8}$ is within the range defined by $[V_1, V_2]$, then the comparator 16 does not issue defect detection signal $S_T$ to the output circuit 19.

The comparator 26 compares the received difference signal $\Delta S_{8-9}$ with reference values $V_3$, $V_4$. If the value of difference signal $\Delta S_{8-9}$ is out of the range of $[V_3, V_4]$, then the comparator 26 sends out confirmation request signal $C_Y$ to a counter 32. The counter 32 decides whether defect detection signal $S_Y$ should be issued or not according to the result of the comparison between the time measured by the clock 34 and preset time $t_0$ as in the case of the third embodiment.

In the fourth embodiment, difference signal $\Delta S_{7-8}$ which is the difference between voltage signals $S_7$ and $S_8$ and difference signal $\Delta S_{8-9}$ which is the difference between voltage signals $S_8$ and $S_9$ almost offset the variation components which have been included in the respective voltage signals. As a result, difference signal $\Delta S_{7-8}$ accurately reflects the presence of a defect in warp yarn T and therefore the comparison between difference signal $\Delta S_{7-8}$ and reference values $V_1$, $V_2$ enhances the accuracy of inspecting warp yarn for a defect.

Furthermore, in difference signal $\Delta S_{8-9}$ which is the difference between voltage signals $S_8$ and $S_9$, the change components which are attributable to disturbances and which have been included in the voltage signals are nearly offset. In addition, since the photoreceptor elements 36, 37 are arranged in series in the direction of warp yarn, the change components in the electric signals caused by the light reflected from the warp yarn are also offset. As a result, difference signal $\Delta S_{8-9}$ accurately reflects the presence of a defect in weft yarn Y and therefore the comparison between difference signal $\Delta S_{8-9}$ and reference values $V_3$, $V_4$ enhances the accuracy of inspecting weft yarn for a defect. Moreover, the pseudo defects can be distinguished from weft yarn defects, resulting in higher accuracy in inspecting weft yarn for defects.

Figure 13:
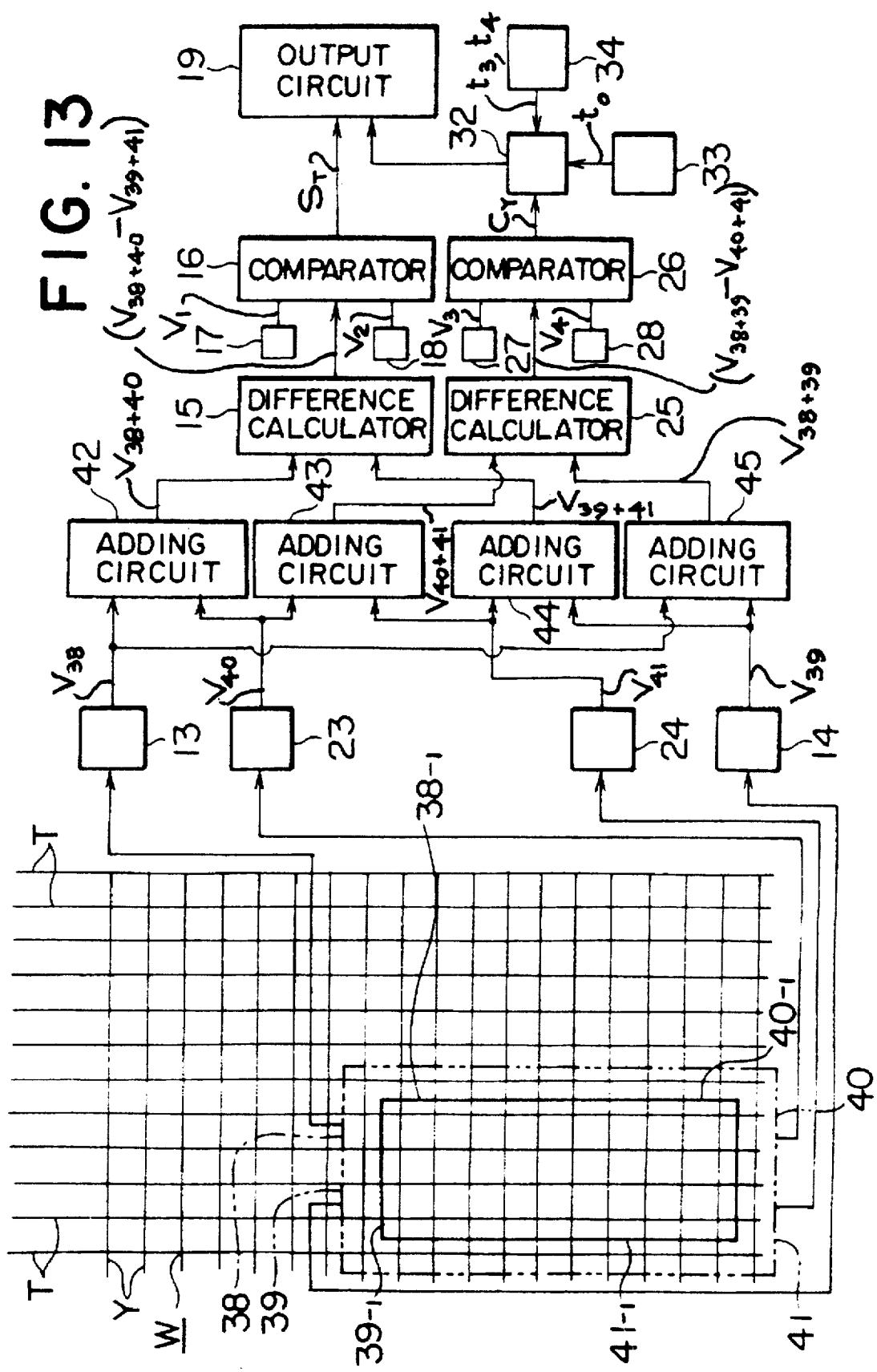
FIG. 13 shows the combination of the control circuit and the detectable range on woven cloth which are illustrative of a fifth embodiment.

The fifth embodiment shown in FIG. 13 will now be described. The same component members as those of the fourth embodiment are given the same reference numerals and detailed description thereof will be omitted. In the fifth embodiment, of the four photoreceptor elements 38, 39, 40, and 41, two each are arranged in series in the direction of warp yarn T and in the direction of weft yarn Y of the woven cloth W. Reference numerals 38-1, 39-1, 40-1, and 41-1 represent the detection ranges of the respective photoreceptor elements 38 through 41. The photoreceptor element 38 supplies the current signal to the current-to-voltage converter 13; the photoreceptor element 39 supplies the current signal to the current-to-voltage converter 14. The photoreceptor element 40 supplies the current signal to the current-to-voltage converter 23; and the photoreceptor element 41 supplies the current signal to the current-to-voltage converter 24. The current-to-voltage converter 13 converts the current signal to a voltage signal which is then supplied to adding circuits 42, 45; and the current-to-voltage converter 14 converts the current signal to a voltage signal which is then supplied to adding circuits 44, 45. The current-to-voltage converter 23 converts the current signal to a voltage signal which is then supplied to adding circuits 42, 43; and the current-to-voltage converter 24 converts the current signal to a voltage signal which is then supplied to adding circuits 43, 44.

All the adding circuits 42 through 45 output sum signals resulting from adding the received voltage signals. The adding circuits 42, 44 send out sum signals to the difference calculating circuit 15; and the adding circuits 43, 45 send out sum signals to the difference calculating circuit 25. If the voltage signal values of the current-to-voltage converters 13, 14, 23, and 24 are taken as $V_{38}$, $V_{39}$, $V_{40}$, and $V_{41}$, then the sum signal values of the respective adding circuits 42 through 45 will be $(V_{38}+V_{40})$, $(V_{40}+V_{41})$, $(V_{39}+V_{41})$, and $(V_{38}+V_{39})$, $V_{38}$, $V_{39}$, $V_{40}$, and $V_{41}$ respectively correspond to the current signals of the photoreceptor elements 38 through 41. The difference calculating circuit 15 subtracts the sum signal value $(V_{39}+V_{41})$ from the sum signal value $(V_{38}+V_{40})$; the difference calculating circuit 25 subtracts the sum signal value $(V_{40}+V_{41})$ from the sum signal value $(V_{38}+V_{39})$.

The difference calculating circuit 15 supplies a difference signal obtained from the arithmetic operation to the comparator 16; the difference calculating circuit 25 supplies the difference signal obtained from the arithmetic operation to the comparator 26. The comparator 16 determines whether it should issue defect detection signal $S_T$) to the output circuit 19 according to the result of the comparison between reference values $V_1$, $V_2$ and difference signal value [$(V_{38}+V_{40})-(V_{39}+V_{41})$]. The comparator 26 determines whether it should issue confirmation request signal $C_Y$) to the counter 32 according to the result of the comparison between reference values $V_3$, $V_4$ and difference signal value [$(V_{38}+V_{39})-(V_{40}+V_{41})$].

The adding circuit 42 combines the photoreceptor elements 38, 40 into one piece; and the adding circuit 43 combines the photoreceptor elements 40, 41 into one piece. Further, the adding circuit 44 combines the photoreceptor elements 39, 41 into one piece; and the adding circuit 45 combines the photoreceptor elements 38, 39 into one piece. This embodiment is designed to take the difference between the voltage signal obtained from the pair of photoreceptor elements, which have been combined into one piece, and the voltage signal obtained from the pair of photoreceptor elements. Hence, this embodiment also enables highly accurate inspection just like the case of the fourth embodiment. Furthermore, the pair of photoreceptor elements arranged in the direction of the warp yarn are integrated and the pair of photoreceptor elements arranged in the direction of the weft yarn are integrated, expanding the detection range both in the warp yarn and weft yarn directions. The expanded detection range adds to the capability of inspecting warp yarn and weft yarn for a defect.

Figure 14:
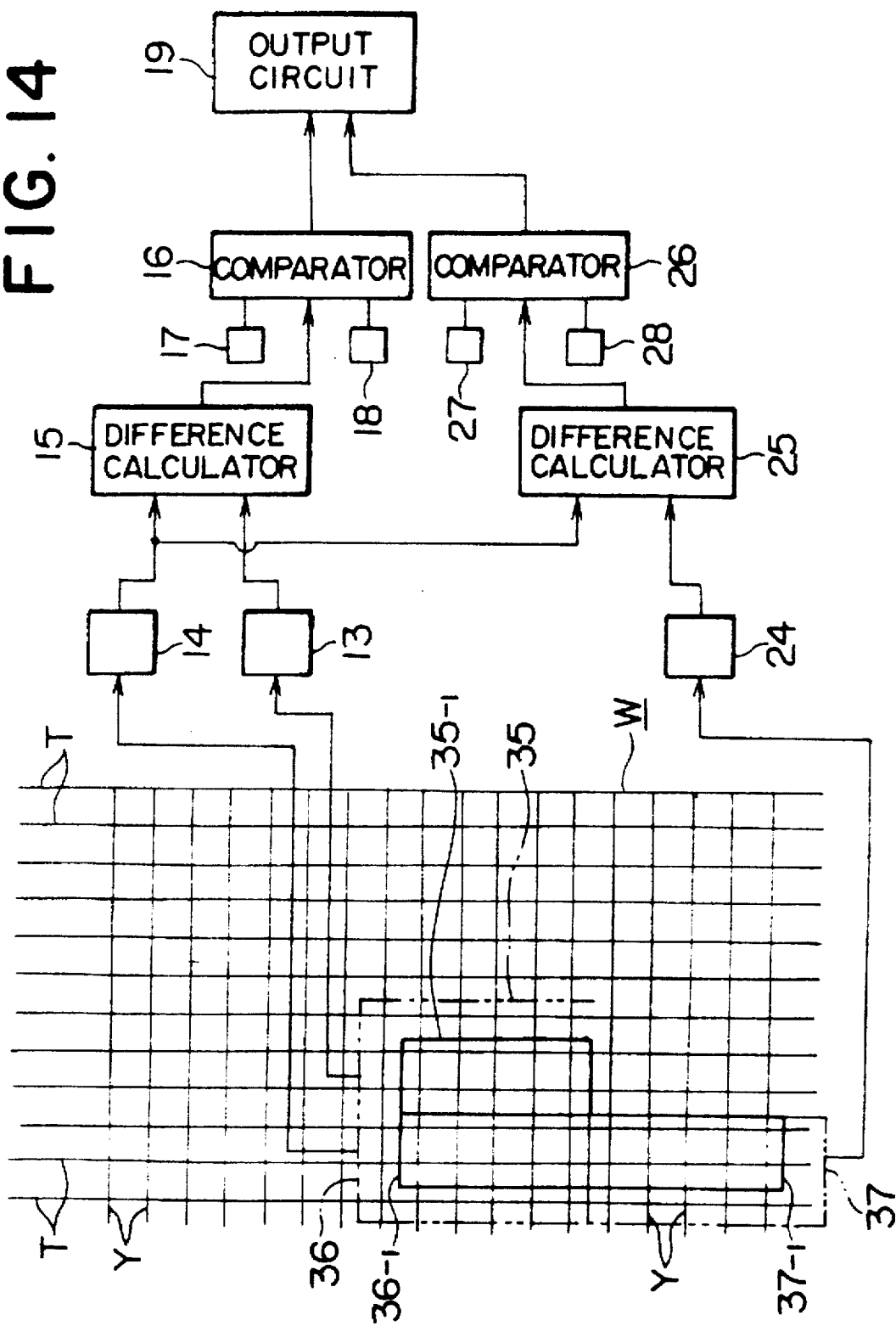
FIG. 14 shows the combination of the control circuit and the detectable range on woven cloth which are illustrative of another example.
Figure 15:
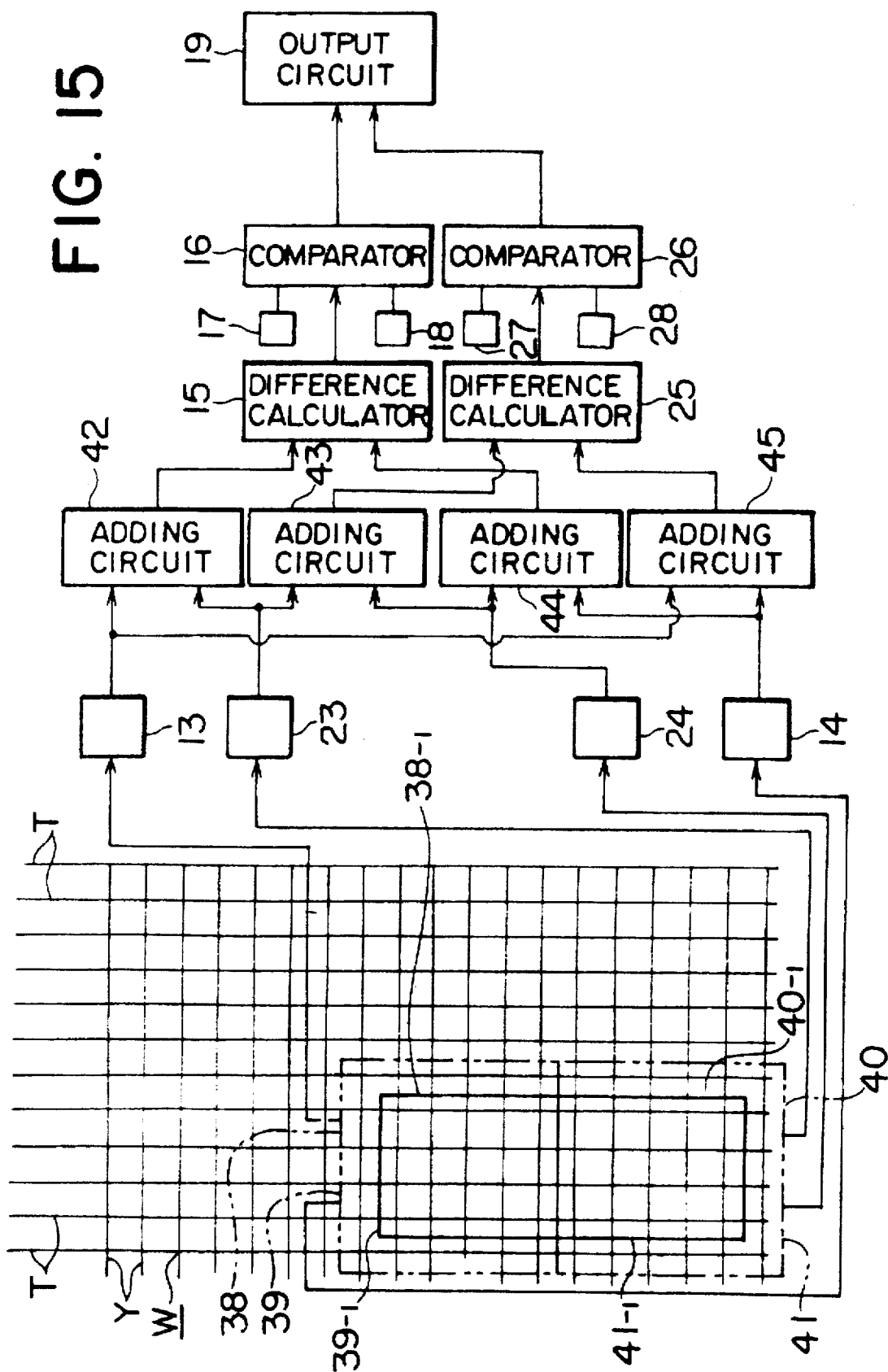
FIG. 15 shows the combination of the control circuit and the detectable range on woven cloth which are illustrative of still another example.

The fourth and fifth embodiments employ the pseudo defect determining means constructed by the counter 32, the latching circuit 33, and the clock 34; however, the pseudo defect determining means may be omitted as shown in the embodiments of FIGS. 14 and 15. The embodiments shown in FIGS. 14 and 15 are also capable of eliminating the influences of disturbances and of achieving highly accurate inspection of woven cloth.

Figure 16:
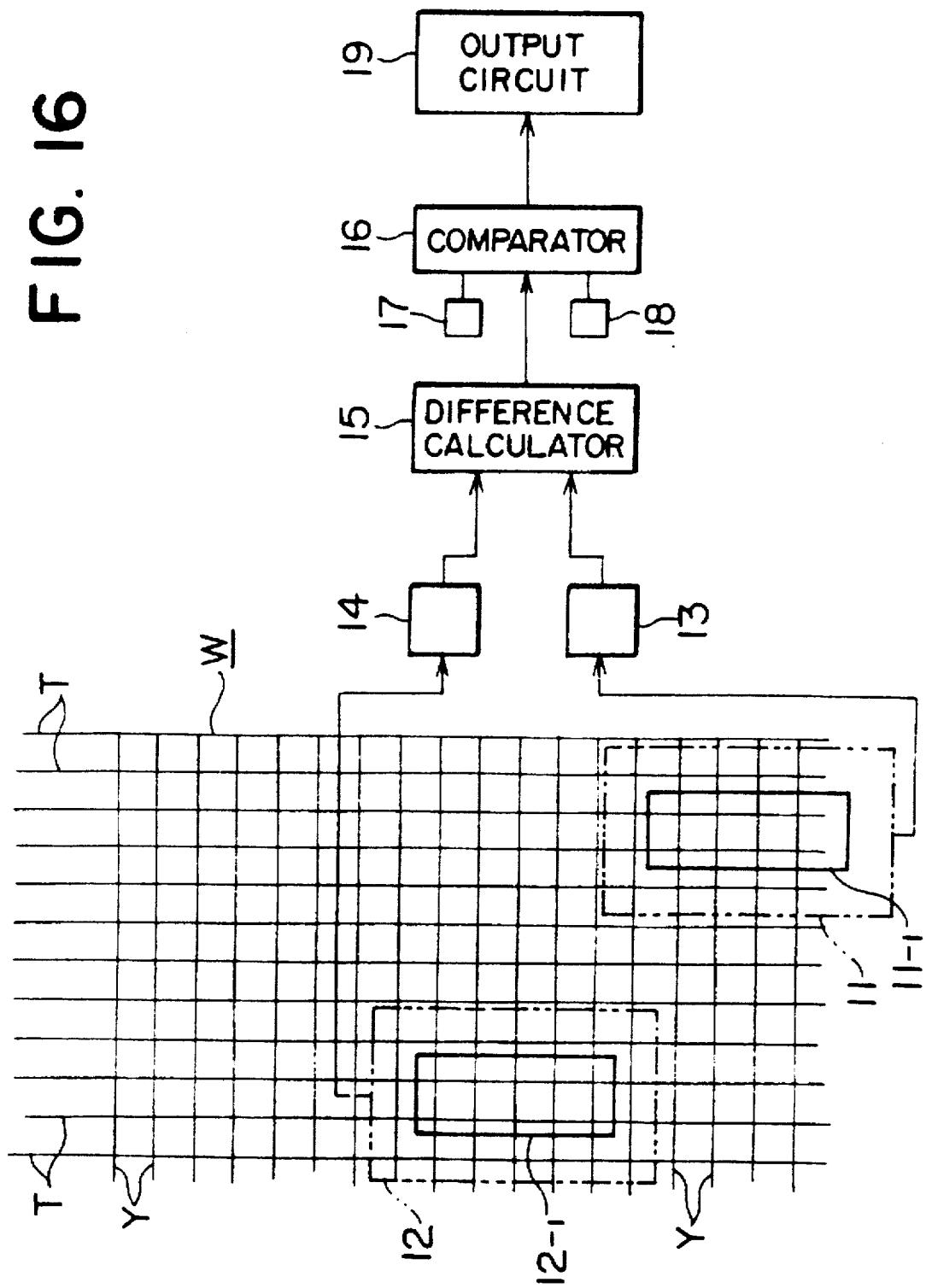
FIG. 16 shows the combination of the control circuit and the detectable range on woven cloth which are illustrative of a further example.
Figure 17:
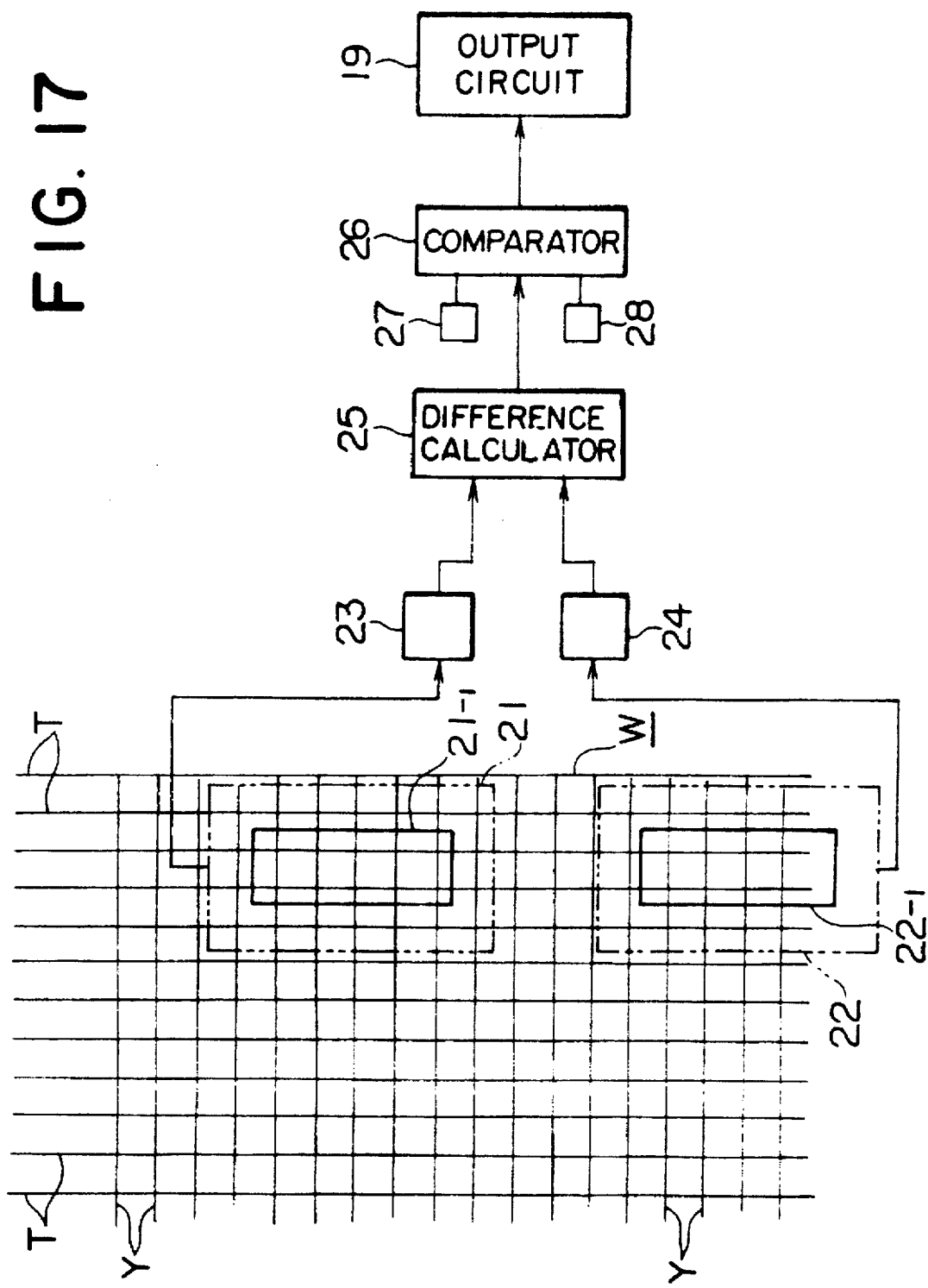
FIG. 17 shows the combination of the control circuit and the detectable range on woven cloth which are illustrative of a still further example.

In the present invention, to inspect warp yarn for a defect, the photoreceptor elements 11, 12 may be positioned apart from each other both in the direction of warp yarn T and weft yarn Y as shown in FIG. 16. Likewise, the photoreceptor elements 21, 22 may be positioned apart from each other in the direction of warp yarn T as shown in FIG. 17 when inspecting weft yarn for a defect.

Figure 18:
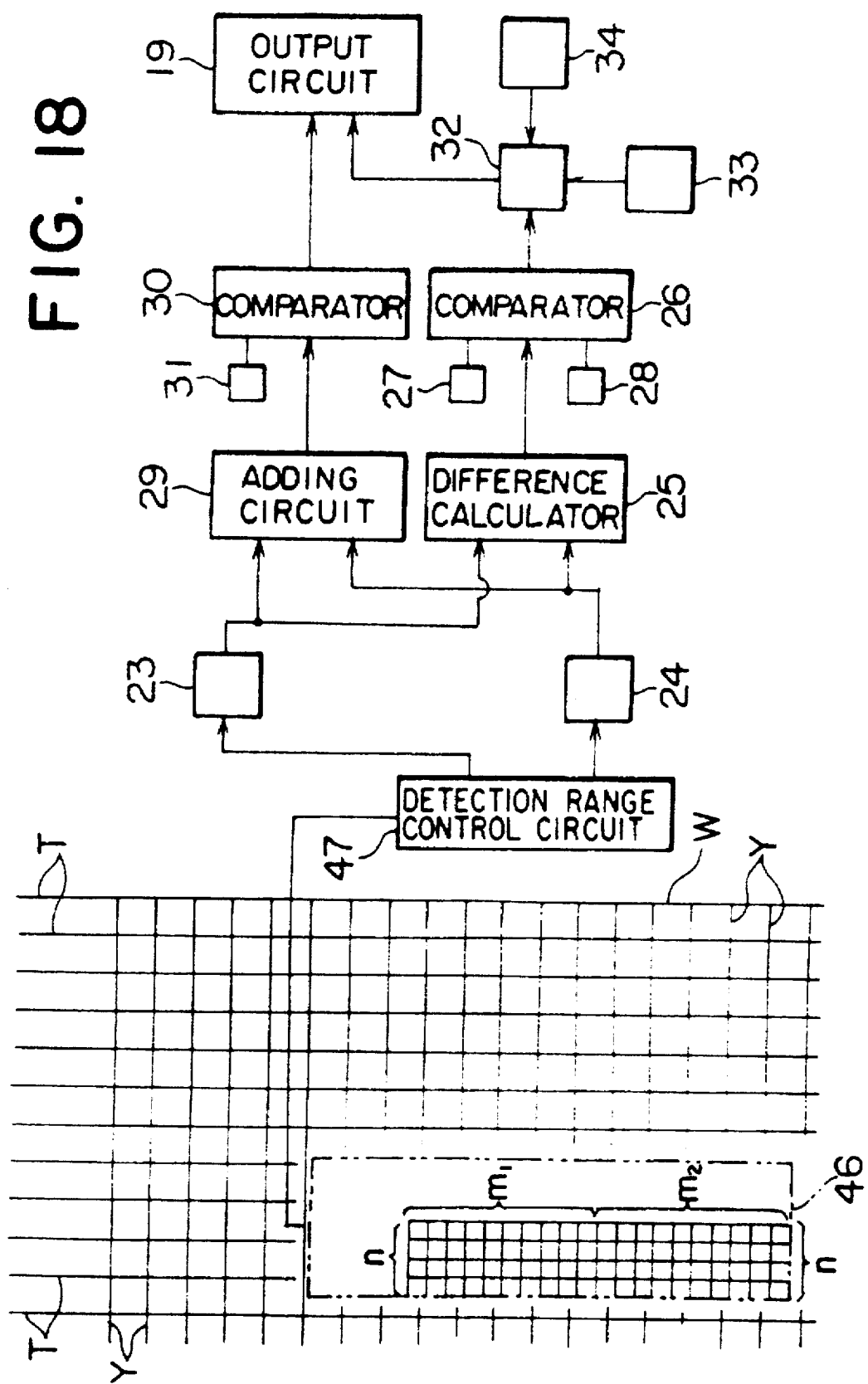
FIG. 18 shows the combination of the control circuit and the detectable range on woven cloth which are illustrative of yet another example.

As the photoelectric sensor, an image sensor 46 shown in FIG. 18 may be employed. The size of the detection range can be selected by using an appropriate number of picture elements out of all picture elements of the image sensor 46, so that the same single relative moving velocity $V_Y$ of the image sensor may be set even for the inspection wherein pseudo defects are distinguished from weft yarn defects. More specifically, relative moving velocity $V_Y$ is preset and width $L_Y$ in the direction of weft yarn and width $L_T$ in the direction of warp yarn in the detection range are set according to the equations (1) to (6) given above. Setting such relative moving velocity $V_Y$ improves the efficiency in preparing for inspection of the woven cloth.

In the drawing, FIG. 18, the detection range indicated by $(n, m_1)$ corresponds to detection range 21-1 of the embodiment shown in FIG. 9; the detection range indicated by $(n, m_2)$ corresponds to detection range 22-1 of the embodiment shown in FIG. 9. The converted current of detection range $(n, m_1)$ is sent to the current-to-voltage converter 23 through a detection range control circuit 47; and the converted current of detection range $(n, m_2)$ is sent to the current-to-voltage converter 24 through the detection range control circuit 47. The subsequent signal processing is the same as that of the third embodiment.

In place of the picture elements of the image sensor, a small photodiode or phototransistor may be used. Further, three or more photoreceptor elements may be arranged in the warp yarn or weft yarn direction and the electric signals which are obtained from the photoreceptor elements arranged in the warp yarn or weft yarn direction may be added, so that the photoreceptor elements arranged in the warp yarn or weft yarn direction may be combined into one piece.

In all the embodiments described above, the sensor head moves in the direction of the width of the woven cloth. As an alternative, for the purpose of inspecting weft yarn for defects, the apparatus for inspecting the woven cloth may have a plurality of light receiving sensors which are fixed at appropriate intervals in the direction of the width of the woven cloth. Likewise, for the purpose of inspecting warp yarn for defects, the apparatus for inspecting the woven cloth may have, for example, image sensors which are fixed continuously all over the width of the woven cloth.

In the embodiments stated above, the apparatus for inspecting woven cloth is mounted on the weaving machine; however, the method and apparatus for inspecting woven cloth in accordance with the present invention can be applied to an inspection performed on woven cloth which has been removed from the weaving machine.

Further according to the present invention, the presence of issued defect detection signals $S_T$, $S_Y$ or the presence of confirmation request signal $C_Y$ are stored in a memory, so that the stored data can be used to evaluate the quality of the woven cloth or to manage the weaving machines.

The following describes the aspects and advantages of the present invention. The apparatus for inspecting woven cloth with a photoelectric sensor may employ image sensors for the photoelectric sensors.

The same single moving velocity of the image sensor in the direction of the width of the woven cloth may be set even for the inspection wherein pseudo defects are distinguished from weft yarn defects.

Thus, according to one aspect of the present invention, the plurality of photoelectric sensors are disposed in the direction of either the warp yarn or the weft yarn. The difference between the electric signal from at least one of the photoelectric sensors and the electric signal from the other electric sensors is calculated in order to eliminate the changes in the electric signal caused by disturbances. This permits highly accurate inspection of the woven cloth.

According to another aspect of the present invention, the difference between the electric signal from at least one of the plurality of photoelectric sensors disposed in the direction of warp yarn and the electric signal from another photoelectric sensor is calculated and the sum of the electric signals from the photoelectric sensors is also calculated. This eliminates the changes in the electric signals related to weft yarn attributable to disturbances and also improves the capability of inspecting warp yarn for defects by the expanded detection range.

According to still another aspect of the present invention, the pseudo defect determining means allows weft yarn defects to be distinguished from pseudo defects, making it possible to avoid an inspection error caused by a pseudo defect.

What is claimed is:

1. A method for inspecting cloth having length and width woven with lengthwise warp yarn and filling weft yarn by using photoelectric sensors for scanning the cloth surface and providing electric signals based on the amount of light received by said sensors to detect any defects present in the woven cloth, said method comprising the steps of:

disposing a plurality of said photoelectric sensors in an array in the direction of one of said yarns selected from said warp and weft yarns for simultaneously scanning different areas of said cloth encompassing a plurality of adjacent yarns, and causing relative movement between said sensors and said cloth to cause the expanse of said cloth to be scanned by said sensors;

calculating the difference between said electric signals from at least a first and a second of said plurality of photoelectric sensors; and determining based upon said calculated difference whether a defect detection signal should be issued indicative of a defect in the warp or weft yarns that are other than said selected one of said yarns.

2. A method for inspecting cloth woven with warp yarn and weft yarn according to claim 1, wherein said photoelectric sensors are disposed in the direction of said warp yarn and said defect detection signal is indicative of a defect in said weft yarn.

3. A method for inspecting cloth woven with warp yarn and weft yarn according to claim 1, wherein said photoelectric sensors are disposed in the direction of said weft yarn and said defect detection signal is indicative of a defect in said warp yarn.

4. Apparatus for inspecting cloth having length and width woven with lengthwise warp yarn and filling weft yarn in which photoelectric sensors are used for scanning the cloth surface and providing electric signals based on the amount of light received by said sensors to detect any defects present in the woven cloth, said apparatus comprising:

a plurality of said photoelectric sensors disposed in an array in the direction of one of said yarns selected from said warp and weft yarns for simultaneously scanning different areas of said cloth;

means for causing relative movement between said sensors and said cloth to scan the expanse of said cloth with said sensors thereby providing said electric signals;

means for calculating the difference between said electric signals from at least a first and a second of said plurality of photoelectric sensors; and means for determining based upon said calculated difference whether a defect detection signal should be issued indicative of a defect in the warp or weft yarns that are other than said selected one of said yarns.

5. Apparatus for inspecting cloth woven with warp yarn and weft yarn in which photoelectric sensors are used for scanning the cloth surface and providing electric signals based on the amount of light received by said sensors to detect any defects present in the woven cloth, said apparatus comprising:

a plurality of said photoelectric sensors disposed in the direction of said warp yarn for simultaneously scanning different areas of said cloth;

means for causing relative movement between said sensors and said cloth to scan the expanse of said cloth with said sensors thereby providing said electric signals;

means for calculating the difference between said electric signals from at least a first and a second of said plurality of photoelectric sensors;

adding means for calculating the sum of the electric signals from said plurality of photoelectric sensors;

means for determining based upon said calculated sum whether a defect detection signal should be issued indicative of a defect in said warp yarn; and means for determining based upon said calculated difference whether a defect detection signal should be issued indicative of a defect in said weft yarn.

6. Apparatus for inspecting cloth woven with warp yarn and weft yarn in which photoelectric sensors are used for scanning the cloth surface and providing electric signals based on the amount of light received by said sensors to detect any defects present in the woven cloth, said apparatus comprising:

a plurality of said photoelectric sensors disposed in the direction of said warp yarn and mounted for movement in the width direction of said woven cloth for simultaneously scanning different areas of said cloth thereby providing said electric signals;

means for moving said plurality of sensors across the width of said woven cloth;

means for calculating the difference between said electric signals from at least a first and a second of said plurality of photoelectric sensors and providing a difference signal proportional to said difference;

adding means for calculating the sum of the electric signals from said plurality of photoelectric sensors;

means for determining based upon said calculated sum whether a defect detection signal should be issued indicative of a defect in said warp yarn;

means for comparing the magnitude of said difference signal with the magnitude of a reference signal and providing a time width fixation signal corresponding to said difference signal when said magnitude of said difference signal exceeds said magnitude of said reference signal; and pseudo defect determining means for determining based upon the time width of said time width fixation signal whether a defect detection signal should be issued indicative of a defect in said weft yarn.

7. Apparatus for inspecting cloth woven with warp yarn and weft yarn in which photoelectric sensors are used for scanning the cloth surface and providing electric signals based on the amount of light received by said sensors to detect any defects present in the woven cloth, said apparatus comprising:

a plurality of said photoelectric sensors of which at least two sensors are disposed in each of the warp and weft directions mounted for movement in the width direction of said woven cloth for simultaneously scanning different areas of said cloth thereby providing said electric signals;

means for moving said plurality of sensors across the width of said woven cloth;

first difference calculating means for calculating the difference between said electric signals from a first and a second of said plurality of photoelectric sensors that are disposed in said weft direction and providing a first difference signal proportional to said difference calculated by said first calculating means;

second difference calculating means for calculating the difference between said electric signals from a first and a second of said plurality of photoelectric sensors that are disposed in said warp direction and providing a second difference signal proportional to said difference calculated by said second calculating means;

means for determining based upon said first difference signal whether a defect detection signal should be issued indicative of a defect in said warp yarn;

means for comparing the magnitude of said second difference signal with the magnitude of a reference signal and providing a time width fixation signal corresponding to said second difference signal when said magnitude of said second difference signal exceeds said magnitude of said reference signal; and pseudo defect determining means for determining based upon the time width of said time width fixation signal whether a defect detection signal should be issued indicative of a defect in said weft yarn.

* * * * *

UNITED STATES PATENT AND TRADEMARK OFFICE
CERTIFICATE OF CORRECTION

PATENT NO.   : 5,694,979
DATED        : December 9, 1997
INVENTOR(S)  : Masashi Toda It is certified that error appears in the above-indentified patent and that said Letters Patent is hereby corrected as shown below:

```
In the Abstract: line 5, change "area" to --areas--;
Col. 2, line 8, change "ward" to --warp--;
Col. 5, line 54, after "S₁" cancel the comma (,);
Col. 5, line 59, after "E₄" insert a comma (,);
Col. 6, line 8, after "E₂₋₁" cancel the comma (,);
Col. 6, line 15, change "yarn" to --yarns--;
Col. 6, line 16, change "yarn" to --yarns--;
Col. 7, line 8, change "Q₁" to --Q̲₁--;
Col. 7, line 53, change "T" (first occurrence) to --Y--;
Col. 9, line 66, after "and" (second occurrence)
       insert --if--;
Col. 10, line 42, after "Curve" insert --E₁--;
```

Signed and Sealed this

Eleventh Day of August 1998

*Attest:*

BRUCE LEHMAN

*Attesting Officer*   Commissioner of Patents and Trademarks